United States Patent
Dukoff

(10) Patent No.: US 10,925,895 B2
(45) Date of Patent: *Feb. 23, 2021

(54) COMPOSITION AND METHOD OF USING MEDICAMENT FOR TREATMENT OF CANCERS AND TUMORS

(71) Applicant: Amy Dukoff, New York, NY (US)

(72) Inventor: Amy Dukoff, New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 16/662,146

(22) Filed: Oct. 24, 2019

(65) Prior Publication Data
US 2020/0113935 A1 Apr. 16, 2020

Related U.S. Application Data

(63) Continuation of application No. 14/637,435, filed on Mar. 4, 2015, now Pat. No. 10,463,692.

(60) Provisional application No. 61/949,618, filed on Mar. 7, 2014.

(51) Int. Cl.
| | | |
|---|---|---|
| *A61K 33/08* | (2006.01) | |
| *A61K 33/00* | (2006.01) | |
| *A61K 31/19* | (2006.01) | |
| *A61K 31/17* | (2006.01) | |

(52) U.S. Cl.
CPC .............. *A61K 33/08* (2013.01); *A61K 31/17* (2013.01); *A61K 31/19* (2013.01); *A61K 33/00* (2013.01)

(58) Field of Classification Search
CPC ........ A61K 31/17; A61K 31/19; A61K 33/00; A61K 33/08
See application file for complete search history.

(56) References Cited

U.S. PATENT DOCUMENTS

| | | | | |
|---|---|---|---|---|
| 2011/0046041 | A1* | 2/2011 | Neesham-Grenon | ........................ A61K 38/14 514/3.1 |
| 2014/0309308 | A1* | 10/2014 | Evison | ..................... A61K 8/44 514/565 |

FOREIGN PATENT DOCUMENTS

WO    WO-2007094999 A3 * 11/2008 ........... A61K 8/4926

OTHER PUBLICATIONS

Rouse et al., "A Review of Keratin-Based Biomaterials for Biomedical Application," Materials 2010, 3, pp. 999-1014, doi:10.3390/ma3o20999; retrieved from www.mdpi.com/journal/materials on Mar. 4, 2015.
"Bone," retrieved from http://en.wikipedia.org/wiki/Bone on Jul. 5, 2012, 7 pages.
Balto, Khaled A., "Calcium hydroxide has limited effectiveness in eliminating bacteria from human root canal," Evidence Based Dentristry (2007) 8, 15-16; King Abdulaziz University, Jeddah, Saudi Arabia; retrieved from http://www.nature.com/ebd/journal/v8/n1/full/6400467a.html on Mar. 4, 2015, 4 pages.
"Cetearyl Alcohol NF," retrieved from http://www.ingredientstodiefor.com/item/Cetearyl_Alcohol_NF-30_70_Blend_150; on Mar. 4, 2015, 1 page.
"Chemical Depilatory," retrieved from http://en.wikipedia.org/wiki/Chemical_depilatory; last updated: Feb. 15, 2012, 2 pages.
Sullivan et al., "Cleaning and Preserving Animal Skulls," The University of Arizona Cooperative Extension, retrieved from ag.arizona.edu/pubs/naturesources/az1144.pdf, Oct. 1999, on Mar. 4, 201, 4 pages.
"Dental Pulp Stem Cells," retrieved from http://en.wikipedia.org/wiki/Dental_pulp_stem_cells, last updated: Jun. 8, 2011.
"Disulfide Bond," retrieved from http://en.wikipedia.org/wiki/Disulfide_bond—last updated: Apr. 8, 2012.
"Hair follicle," retrieved from http://en.wikipedia.org/wiki/Hair_follicle—last updated: Mar. 26, 2012.
Synthes, "Reamer/Irrigator/Aspirator (RIA) for intramedullary reaming and bone harvesting".
"Keratin," retrieved from http://www.bio-medicine.org/biology-definition/Keratin/ on Mar. 4, 2015.
"Nair (hair removal)," retrieved from http:...en.wikipedia.org/wiki/Nair_%28hair_removal%29—last updated: Jan. 30, 2012.
"Smear Layer," retrieved from http://en.wikipedia.org/wiki/Smear_layer—last updated: Dec. 23, 2011.
"Sodium Hydroxide," retrieved from http://en.wikipedia.org/wiki/Sodium_hydroxide—last updated: Mar. 2, 2012.
"Sodium Hypochlorite, " retrieved from http://en.wikipedia.org/wiki/Sodium_hypochlorite—last updated: Apr. 6, 2012.
Di Justo, Patrick, "What's Inside: Nair Hair Remover, Feel the Burn!." retrieved from http://www.wired.com/science/discoveries/magazine/16-01/st_nair, Wired Magazine: Issue 16.01, Dec. 2007, 3 pages.
Ghosh, Ritwik, "Average Cost of Cancer Chemotherapy," Livestrong, Aug. 16, 2013, retrieved on Dec. 9, 2016, available at: http://www.livestrong.com/article/389405-what-foods-to-eat-for-an-inflamed-stomach-lining.
Di Nubile. M.J., et al.. "Invasive Candidiasis in cancer patient: observation from a randomized clinicai trial." J. Infect., Jun. 2005, 50(5):443-9, retrieved on May 17, 2016, avail. at: http://www.ncbi.nlm.nih.gov/pubmed/15907554.

(Continued)

*Primary Examiner* — Robert A Wax
*Assistant Examiner* — Olga V. Tcherkasskaya
(74) *Attorney, Agent, or Firm* — Thomas A. O'Rourke; Bodner & O'Rourke, LLP

(57) ABSTRACT

The composition includes a chemical depilatory that may be used in a method of destroying cancer and/or tumor cells and removing the resulting debris from the body. The composition includes thioglycolate and is directly applied to the cancer and/or tumor target cells to interrupt and disable their functioning. This method is unique because it enables the composition to affect the cancer and/or tumor cells without being transported by a carrier through the body to them. This anti-cancer and anti-tumor treatment not only targets the abnormal cells, but also eradicates the microorganisms in the tissue at the target site, which prevents the abnormal growth from recurring due to the presence of residual microorganisms that may trigger formation of dysplastic cells.

7 Claims, 9 Drawing Sheets

(56) References Cited

OTHER PUBLICATIONS

Kubota, Hiroyuki, "Detection of Human Intestinal Catalase-Negative ,Gram-Positive Cocci by rRNA-Targeted Reverse Transcription-PCR," Appl. Environ. Microbial, Aug. 2010, vol. 76, No. 16, 5440-5451, retrieved on May 9, 2017, avail. at: http://aem.org/content/76/16/5440.full.
Park, Alice, "A Surprising Link Between Bacteria and Colon Cancer." TIME, Oct. 18, 2011, retrieved on Dec. 9, 2016, avail. at: http://healthland.time.com/2011/10/18/a-surprising-link-between-bacteria-and-colon-cancer.
Li, Maolin, et al., "Intercapsomeric Disulfide Bonds in Papillomavirus Assembly and Disassembly," J. Virology, Mar. 1998, vol. 72, No. 3, 2160-2167, retrieved on Dec. 9, 2016, avail. at http://jvi.asm.org/content/72/3/2160.full.
Ghoneum, M., "Phagocytosis of Candida Albicans by Metastatic and Non Metastatic Human Breast Cancer Cell Lines In Vitro," Cancer Detect. Prev. 2004, vol. 28, No. 1, pp. 17-26, retrieved on: May 17, 2016, avail. at: http://www.ncbi.nlm.nih.gov/pubmed/15041073.
Kojima. Ayuchi, et al., "Infection of Specific Strains of *Streplococcus mutans*, Oral Bacteria, Confers a Risk of Ulcerative Colitis," Scientific Reports 2012 26.2:332, E pub Mar. 26, 2012, Dept. of Pediatric Dentistry, Grad. School of Dentistry, Osaka Univ., Osaka 565-0871, Japan, retrieved on May 17, 2016, avail. at: http://www.ncbi.nlm.nih.gov/pmc/articles/pmc3312205, 11 pages.
Spectrum chemicals and laboratory products. "Material Safety Data Sheet—Potassium Thioglycolate, 42 Percent Aqueous Solution," retrieved on Mar. 4, 2015, avail. at: https://www.spectrumchemical.com/MSDS/P2105X.pdf.
Jahequi, "Cysteine Cathepsins in Human Dentin-Pulp Complex," retrieved on Mar. 4, 2015, avail. at: http://scienceindex.com/stories/495642/Cysteine_Cathepsins_in_Human_DentinPulp_Complex.html. 2 pages.
"Hair Remover," retrieved on Mar. 4, 2015, avail. at: http://www.madehow.com/Volume-4/Hair-Remover.html, 6 pages.
"How MSM Works to Improve Joint Health," retrieved on Mar. 4, 2015, avail. at: http://www.msmguide.com/jointpain/improvejointhealth/. 1 page.
"Mineral Oil," retrieved on Mar. 4, 2015, avail. at: http://en.wikipedia.org/wiki/Mineral_oil, 6 pages.
"Neurokeratin," retrieved on Mar. 4, 2015, avail at: http://dictionary.reference.com/browse/neurokeratin. 1 page.
Sedamo, Heddie, "Odontogenic Cyst," retrieved on Mar. 4, 2015, avail. at: http://www.dent.ucla.edu/pic/visitors/Cysts/page1.html, 4 pages.
"Peripheral Nerve" retrieved on Mar. 4, 2015, avail. at: http://vanatcvm.umn.edu/neurLab1/nerves.html. 1 page.
"What are the Ingredients in Nair," retrieved on Mar. 3, 2015, avail. at: http://www.ehow.com/about_4571104_what-ingredients-nair.html, 1 page.
"Why You Need Protein in Your Diet" retrieved on Mar. 4, 2015, avail. at: http://www.dummies.com/how-to/content/why-you-need-protein-in-your-diet.html, 2 pages.
CDC, "What Patients Should Know When They are Diagnosed with Genital Warts." retrieved on Mar. 4, 2015, avail. at: http://stdtoolkit.srhd.org/documents/hpv/What_Patients_Should_Know_Warts.pdf, 2 pages.
MDPI: [online]; [retrieved on Mar. 4, 2015]; URL-http://www.mdpi.com/journal/materials. pp. 999-1014: Rouse et al., "A Review of Keratin-Based Biomaterials for Biomedical Application," Materials 2010, 3, doi:10.3390/ma3o20999.
Wikipedia: Bone [online]; [retrieved on Jul. 5, 2012]: URL-http://en.wikipedia.org/wiki/Bone, 7 pages.
Nature: [online]; [retrieved on Mar. 4, 2015]: URL-http://www.nature.com/ebd/journal/v8/n1/full/6400467a.html. 4 pages: Balto, Khaled A., "Calcium hydroxide has limited effectiveness in eliminating bacteria from human root canal," Evidence Based Dentistry (2007) 8, 16-16; King Abdulaziz University, Jeddah, Saudi Arabia.
Ingredients to Die For: [online]; [retrieved on Mar. 4, 2015]; URL-http://www.ingredientstodiefor.com/item/Cetearyl_Alcohol_NF-30_70_Blend_150; on Mar. 4, 2015. 1 page; "Cetearyl Alcohol NF".
Wikipedia: [online]; [retrieved on Feb. 15, 2012], URL-http://en.wikipedia.org/wiki/Chemical_depilatory, 2 pages; "Chemical Depilatory".
Kim et al., "Chemical interaction of alexidine and sodium hypochlorite," Journal of Endodontics, vol. 38, No. 1, Jan. 2012, pp. 112-116, Department of Conservation Dentistry. Dental Research Institute, School of Dentistry, Seoul National University Dental Hospital, Seoul, South Korea.
The University of Arizona Cooperative Extension: [online]; [retrieved on Mar. 4, 2015]; URL-http://g.arizona.edu/pubs/naturesources/az1144.pdf. Oct. 1999, 4 pages; Sullivan et al., "Cleaning and Preserving Animal Skulls".
Gomez, "Dental Pulp Sensory Function.Pain," E.J.E.R. Electronic Journal of Endodontics Rosario, Ano 2010, vol. 02. Oct. 2011.
Wikipedia: [online]; [retrieved on Jun. 8, 2011]; URL-http://en.wikipedia.org/wiki/Dental_pulp_stem_cells. 3 pages; "Dental Pulp Stem Cells".
Rouse et al., "A Review of Keratin-Based Biomaterials for Biomedical Application," Materials 2010, 3, pp. 999-1014.
Wikipedia: Bone [online]; [retrieved on Jul. 5, 2012]; Retrieved from Internet URL: http://en.wikipedia.org/wiki/Bone. (7 pages).
Balto, "Calcium hydroxide has limited effectiveness in eliminating bacteria from human root canal," Evidence Based Dentistry (2007) 8, pp. 15-16.
Ingredients to Die for Aroma Alternatives Limited Co.; "Cetearyl Alcohol NF" [online]; [retrieved on Mar. 4, 2015]; URL:: http://www.ingredientstodiefor.com/item/Cetearyl_Alcohol_NF-30_70_Blend_150; on Mar. 4, 2015. (1 page).
Wikipedia: "Chemical Depilatory" [online]; [retrieved on Feb. 15, 2012]; URL: http://en.wikipedia.org/wiki/chemical_depilatory. (2 pages).
Kim et al., "Chemical interaction of alexidine and sodium hypochlorite," Journal of Endodontics, vol. 38, No. 1, Jan. 2012, pp. 112-116.
Sullivan et al., "Cleaning and Preserving Animal Skulls," The University of Arizona Cooperative Extension; Oct. 1999. (4 pages).
Gomez, "Dental Pulp Sensory Function.Pain," E.J.E.R. Electronic Journal of Endodontics Rosario, Ano 2010, vol. 02, Oct. 2011, pp. 540-554.
Wikipedia: "Dental Pulp Stem Cells" [online]; [retrieved on Jun. 8, 2011]; URL: http://en.wikipedia.org/wiki/Dental_pulp_stem_cells. (3 pages).
Lindsay, "Discussion on Dental Structures and Dental Caries," Section of Odontology, Proceedings of the Royal Society of Medicine, Apr. 8, 1946, vol. 637, Sectional p. 21.
Abd-Elmeguid et al., "Dentin matrix protein-1 activates dental pulp fibroblasts," J. Endod. 2012;38(1):75-80.
Wikipedia: "Disulfide Bond," [online]; [retrieved on Apr. 8, 2012]; URL: http://en.wikipedia.org/wiki/Disulfide_bond—last.
Kara et al., "Effect of different final irrigation solutions on dentinal tubule penetrations depth and percentage of root canal sealer," J. Endod. Jun. 2012:38(6):860-3.
Wikipedia: "Hair follicle," [online] [retrieved on Mar. 26, 2012]; URL: http://en.wikipedia.org/wiki/Hair_follicle.
Dutner et al., "irrigation trends among American Association of Endodontists members: a web-based survey," J. Endod. 2012;38:37-40.
Bio-Medicine; "Keratin," [online] [retrieved on Mar. 4, 2015]; URL: http://www.bio-medicine.org/biology-definition/Keratin/.
Yang et al., "Lipopolysaccharide-induced dental pulp cell apoptosis and the expression of BAX and Bcl-2 in vitro," Braz. J. Med. Biol. Res., vol. 43, 1027-1033.
Peng et al., "Mesenchyma stem cells and tooth engineering," In: J. Oral Sci., 1:6-12 doi:10.4248/ijos.08032 (2009).
Quah et al., "N-acetylcysteine inhibits growth and eradicates biofilm of Enterococcus faecalis," J. Endod., vol. 38, No. 1, Jan. 2012, pp. 81-85.

(56) References Cited

OTHER PUBLICATIONS

Wikipedia; "Nair (hair removal)," [online] [retrieved on Jan. 30, 2012]; URL: http://en.wikipedia.org/wiki/Nair_%28hair_removal%29.

Shakhova et al., "Neural crest-derived stem cells," StemBook ed. The Stem Cell Research Community, pp. 1-17.

Kandaswamy et al., "Root canal irrigants," J. Conserv. Dent. Oct.-Dec. 2010, 13(4): pp. 256-264.

Qin et a., "Smad 1/5 is involved in bone morphogentic protein-2-induced odontoblastic differentiation in human dental pulp cells," J. Endod.. vol. 38. No. 1, Jan. 2012, pp. 66-71, Dept. of Operative Dentistry & Endodontics, Guanghua School of Stomatology, Sun Yat Sen University, Guangzhou, China.

Wikipedia; "Smear Layer," [online] [retrieved on Dec. 23, 2011]; URL: http://en.wikipedia.org/wiki/Smear_layer.

Wikipedia; "Sodium Hydroxide," [online] [retrieved on Mar. 2, 2012]; URL: http://en.wikipedia.org/wiki/Sodium_hydroxide.

Wikipedia; "Sodium Hypochlorite," [online] [retrieved on Apr. 6, 2012]; URL: http://en.wikipedia.org/wiki/Sodium_hypochlorite.

Plotino et al., "Ultrasonics in endodontic surgery: a review of the literature," J. Endod, vol. 33, No. 2, Feb. 2007, pp. 81-95.

Di Justo, Patrick, "What's Inside: Nair Hair Remover, Feel the Burn!," Wired Magazine: Issue 16.01, Dec. 2007, 3 pages.

Yang et al., "Redox modification of cysteine residues regulates the cytokine activity of HMGB1," Molecular Medicine, vol. 18, No. 3, Mar. 2012, pp. 250-259.

Ghosh, Ritwik, "Average Cost of Cancer Chemotherapy," Livestrong, Aug. 16, 2013, [online] [retrieved on Dec. 9, 2016] URL: http://www.livestrong.com/article/389405-what-foods-to-eat-for-an-inflamed-stomach-lining (19 pgs).

Di Nubile, M.J., et al., "Invasive Candidiasis in cancer patient: observation from a randomized clinical trial." J. Infect., Jun. 2005, 50(5): pp. 443-449.

Kubota, Hiroyuki, "Detection of Human Intestinal Catalase-Negative, Gram-Positive Cocci by rRNA-Targeted Reverse Transcription-PCR," Appl. Environ. Microbial, Aug. 2010, vol. 76, No. 16, pp. 5440-5451.

Park, Alice, "A Surprising Link Between Bacteria and Colon Cancer," Time, Oct. 18, 2011, 3 pgs.

Li, Maolin, et al., "Intercapsomeric Disulfide Bonds in Papillomavirus Assembly and Disassembly," J. Virology, Mar. 1998, vol. 72, No. 3, pp. 2160-2167.

Ghoneum, M., "Phagocytosis of Candida Albicans by Metastatic and Non Metastatic Human Breast Cancer Cell Lines In Vitro," Cancer Detect. Prev. 2004, vol. 28, No. 1, pp. 17-26.

Kojima, Ayuchi, et al., "Infection of Specific Strains of *Streptococcus mutans*, Oral Bacteria, Confers a Risk of Ulcerative Colitis," Scientific Reports 2012 26,2:332, E pub Mar. 26, 2012, Dept. of Pediatric Dentistry, Grad. School of Dentistry, Osaka Univ., Osaka, Japan 565-0871, 11 pages.

Spectrum chemicals and laboratory products, "Material Safety Data Sheet—Potassium Thioglycolate, 42 Percent Aqueous Solution," [online] [retrieved on Mar. 4, 2015]; URL: https://www.spectrumchemical.com/MSDS/P2105X.pdf (6 pgs.).

Jahequi, "Cysteine Cathepsins in Human Dentin-Pulp Complex," [online] [retrieved on Mar. 4, 2015]; URL: http://scienceindex.com/stories/495642/Cysteine_Cathepsins_in_Human_DentinPulp_Complex.html (2 pgs.).

"Hair Remover," [online] [retrieved on Mar. 4, 2015]; URL: http://www.madehow.com/Volume-4/Hair-Remover.html (6 pgs.).

"How MSM Works to Improve Joint Health," [online] [retrieved on Mar. 4, 2015]; URL: http://www.msmguide.com/jointpain/improvejointhealth/ (1 pg).

"Mineral Oil," [online] [retrieved on Mar. 4, 2015]; URL: http://en.wikipedia.org/wiki/Mineral_oil (6 pgs.).

"Neurokeratin," [online] [retrieved on Mar. 4, 2015]; URL: http://dictionary.reference.com/browse/neurokeratin (1 pg.).

Sedamo, Heddie, "Odontogenic Cyst," [online] [retrieved on Mar. 4, 2015]; URL: http://www.dent.ucla.edu/pic/visitors/Cysts/page1.html (4 pgs.).

"Peripheral Nerves," [online] [retrieved on Mar. 4, 2015]; URL: http://vanatcvm.umn.edu/neurLab1/nerves.html (1 pg.).

"What are the Ingredients in Nair," [online] [retrieved on Mar. 4, 2015]; URL: http://www.ehow.com/about_4571104_what-ingredients-nair.html (1 pg.).

"Why You Need Protein in Your Diet," [online] [retrieved on Mar. 4, 2015]; URL: http://www.dummies.com/how-to/content/why-you-need-protein-in-your-diet.html (2 pages).

CDC, "What Patients Should Know When They are Diagnosed with Genital Warts," [online] [retrieved on Mar. 4, 2015]; URL: http://stdtoolkit.srhd.org/documents/hpv/What_Patients_Should_Know_Warts.pdf (2 pgs.).

* cited by examiner

COMPOSITION AND METHOD OF USING MEDICAMENT FOR TREATMENT OF CANCERS AND TUMORS

CROSS-REFERENCE TO RELATED APPLICATIONS

This application is a continuation of U.S. application Ser. No. 14/637,435, filed Mar. 4, 2015, which claims the benefit of U.S. Provisional Application No. 61/949,618, entitled "COMPOSITION AND METHOD OF USING MEDICAMENT FOR TREATMENT OF CANCERS AND TUMORS", filed Mar. 7, 2014, which is incorporated here by reference in its entirety.

BACKGROUND OF THE INVENTION

The Field of the Invention

The present invention includes a composition and method for the treatment of cancers and tumors by disrupting the cells ability to function and regenerate. The embodiment breaks up the disulfide bonds in the cancer cells and tumor cells upon direct contact. This unique method of applying the composition directly on the target cells limiting the side effects of chemotherapy. The embodiment breaks apart the disulfide bond so that the tumor and cancer cells no longer have the ability to function or the ability to regenerate. The present invention is unique in its method of applying the treatment composition to kill cancer and tumor cells predictably along with the microorganisms that are in, attached to, and around the targeted site. This method is novel in its ability to kill cancer and tumor cells effectively, economically, and without causing the unwanted chemotherapeutic side-effects along with killing the microorganisms associated with that specific abnormal growth that is within the target site's tissue.

The Description of the Related Art

For many years, chemotherapy has been a standard of care in treating patients with cancer. The cost of chemotherapy keeps increasing. According to an article by Ritwik Ghosh in Livestrong, Aug. 16, 2013, entitled "Average Cost of Cancer Chemotherapy' the cost of eight weeks of chemotherapy can range from $100 to $30,000", treatment with inexpensive drugs like 5-FU or leucovorin costs around $300 for eight weeks. However, to improve therapeutic effect, these drugs are often used in combination with newer drugs that are typically more expensive. According to Johns Hopkins Health Alerts, addition of the product Bevacizumab (a descriptive name), sold under the trade name Avastin®, and the product Cetuximab, sold under the trade name Erbitux® to 5-FU or leucovorin can push up the cost of the dosing regimen to as much as $30,000 (www.livestrong-.com/article/153376-the-average-cost-for-cancer-chemotherapy-treatment/).

Along with the rising cost of chemotherapy treatment, chemotherapy causes the treated patients harm due to the unwanted side effects of the treatment. The challenges for the patients of using chemotherapy drugs include, but are not limited to, many of these side effects, such as hair loss, vision problems, headaches, loss of balance, hearing loss, fatigue, constipation, memory changes, and diarrhea. Presently, the chemotherapy drugs for treatment of cancer and tumors not only cause deleterious side effects to the patient but also are expensive. Furthermore, the chemotherapy drugs do not totally eradicate the cancer cells or the tumor cells from the patient, since there is a risk of recurrence.

A chemotherapy drug is a drug that travels inside the body to reach its target cells. There are many types of chemotherapeutic drugs that are used for each specific cancer. These cancer therapies include alkylating agents that damage the DNA, antimetabolites that interfere with the DNA and RNA, anthracyclines that interfere with the enzymes in DNA and targeted therapies. All these chemotherapy drugs are associated with side effects, since their treatment requires them to travel in the body in order to reach their target cell site.

Some of the new drugs that are being developed are those that target the disulfide bonds in the cell, since breaking the disulfide bonds in cell disrupts the functioning of cell. The disruption of the disulfide bonds affects the functioning of all cells, which include normal healthy cells and normal cells that are behaving abnormally. The new chemotherapy drugs are prodrugs and antibodies that are utilized as carriers. These chemotherapy drugs target the disulfide bonds in order to disrupt the cell's ability to function just as the present invention does. For example, anti-tumor prodrugs claiming to be cytotoxic to the cancer cells, which are described in EP 0317956 A2, cleave or split the disulfide bonds. Also, according to "Methods for treating cancer using combination therapies", WO 2014 085575 A1, a disulfide bond is released inside the cell with the aid of a thiol inhibitor to increase the effectiveness of the drug against cancer. In "An anti-tumor targeting complex and a preparation method and applications thereof", CN 103288968 A, another drug is described, which targets disulfide bond cross-linking to achieve a good anti-tumor treatment that can be claimed as effective against cancer. Furthermore, the active ingredient described in, "Anti-cancer drugs for the treatment of leukaemia t constituted by the chain a of Ricin and a specific monoclonal antibody", CA 1209472 A, includes a disulfide bridge in the monoclonal antibody. The chemotherapy presently used in the treatment for anti-cancer and anti-tumor therapy utilizes the fact that disrupting the disulfide bonds in cancer and tumor cells is effective against these diseases and abnormal growth of tissues.

Thiol derivatives are considered to have potent and potentially important abilities to inhibit cancer growth and tumor growth. In China, research has been done confirming that thiol derivatives displayed anticancer activity (Molecules 2012, 17,3933-3944;doi: 10/3390/molecules 17043933). Thiol derivatives are used effectively in anti-cancer therapies.

Recent literature has shown that there is an association between bacteria and cancer. Common microbes of the oral flora, such as *Candida albicans, Streptococcus mutans* and *Enterococci faecalis*, are associated with cancer. It was stated that *C. albicans* was the single most frequent isolate in cancer patients, although the majority of cases were caused by non-*albicans* species, Invasive Candidiasis in cancer patients: observations from a randomized clinical trial, DiNubile MJ, Hille D, Sable CA, Kartsonis NA, J Infect. 2005 June;50(5):443-9 Furthermore, it was reported that *Streptococcus mutans* is the leading cause of dental caries (tooth decay) worldwide and is considered to be the most cariogenic of all of the oral streptococci. Genome sequence of *Streptococcus mutans* UA159, a cariogenic dental pathogen, Dragana Ajdiĉ, et al, Proc Natl Acad Sci USA. 2002 Oct. 29; 99(22): 14434-14439. It is a genome sequence of *Streptococcus mutans* UA159, a cariogenic dental pathogen. Also, *Enterococci faecalis* is known by the Society for General Microbiology as the bacteria in the gut that causes cancer. *Enterococcus faecalis* is found in the feces of patients with colorectal cancer, Detection of Human Intestinal Catalase-Negative, Gram-Positive Cocci by rRNA-Targeted Reverse Transcription-PCR, Hiroyuki Kubota, Hirokazu Tsuji, Kazunori Matsuda, Takashi Kurakawa, Takashi Asahara, Koji Nomoto Applied & Environmental Microbiology),Aug. 2010, p. 5440-5451, A recent article in the Time said: "The human papillomavirus, or HPV, is behind many cases of cervical cancer." Also, the article stated, "It's the first time that *Fusobacterium* has been linked to cancer. Time, Oct. 18, 2011, Alice Park, A Surprising Link Between Bacteria and Colon Cancer. The close association of cancer to bacteria is that bacteria produce infectious diseases that are linked to causing cancer. Furthermore, *mycoplasma* bacteria (Progenitor Cryptocides) is known to cause cancer. According to the American Cancer Society, bacteria can cause cancer. Moreover, bacteria can invade and enter the cancer cell forming an infectious cancerous cell. This leads to the development of having antibodies used as the carrier of complexes that when combined with the cancer host cell would cause cell death. Antibodies with therapeutic structures incorporated would cause cell death of the cancer cell. The antibiotics that are engineered to specifically target cancer cells had to travel through the blood stream thus affecting normal cells, which would cause unwanted 'chemo-therapeutic' side effects. According to WO 2014 085575 A1 a thiol inhibitor is used for the treatment of a cancer of inflammation, specifically ovarian cancer. Ovarian cancer is detected by the presence of a microorganism. There is a direct relationship between cancer detection and the presence of microorganisms.

Medical research has proven that cancer can be caused by microorganisms. Rous in 1966 won a Nobel prize for discovering that the RNA virus can cause cancer (Kuper, H., Adami, H.-O. and Trichopoulos, D. (2000), Infections as a major preventable cause of human cancer. Journal of Internal Medicine, 248: 171-183; doi: 10.1046/j, 1365-2796.2000.00742.x!). The US Virus Cancer Program was created to encourage research that focuses on cancers caused by infectious agents. According to the Journal of Internal Medicine, "Infections may be responsible for over 15% of all malignancies worldwide". Important mechanisms by which infectious agents may induce carcinogenesis include the production of chronic inflammation (Kuper, H., Adami, H.-O. and Trichopoulos, D. (2000), Infections as a major preventable cause of human cancer. Journal of Internal Medicine, 248: 171-183; doi: 10.1046/j. 1365-2796.2000.00742.x!).

All present chemotherapies cause deleterious side effects. There are no chemotherapies for the treatment of cancer and tumors that are available that lack harmful side effects for the patient. Furthermore, there are no current anti-cancer and anti-tumor treatments that kill the microorganisms around and in and attached to the growing cancer and tumor cells in order to protect the patient from having the micro-organisms remain to trigger the recurrence of the abnormal cancer or tumor growth. The compositions and methods according to the present invention are novel because they cause cell death of the specific cells at the site or area of the cells without causing harmful side effects to the patient.

Moreover, the present invention uses a known modality of targeting the disulfide bond in cells that causes cell death by a chemical depilatory but with a new use utilizing a new method of administrating the composition. Chemical depilatories weaken hair by affecting its disulfide bonds in keratin, facilitating its removal from the skin. The disulfide bond is weaker than the C—C and C—H bonds. Thus, the disulfide bond is referred to as the "weak link". U.S. Pat. No. 6,425,891 discloses removal of unwanted hair on the body with a thioglycolate depilatory composition, which breaks the disulfide bonds in the keratin of the hair. The disulfide bonds are located between cysteine groups in the keratin of the hair. Breaking the disulfide bonds in the hair allows the hair to be easily wiped away. Disulfide bonds are present in bacteria and serve a protective role for the bacteria. Secondly, in humans, disulfide bonds are mostly found in secretory proteins, lysosomal proteins, and the exoplasmic domains of stability of proteins in the extracellar tissue. Thirdly, disulfide bonds are found in the neurokeratin of the myelinated sensory nerve A fibers. Lastly, disulfide bonds are present in HNGB1 (high-mobility group protein-1), which is a mediator of inflammation. Disulfide bonds are the 'glue' that hold together molecules and proteins. When disulfide bonds are broken, it weakens and breaks down the structure facilitating its removal from the target site (US U.S. Pat. No. 8,961,180 by Dr. Amy Dukoff; COMPOSITION AND METHOD OF USING MEDICAMENT FOR ENDODONTIC IRRIGATION, STEM CELL PREPARATIONS AND TISSUE REGENERATION).

Currently, all the present chemotherapies are administered orally, intramuscularly, sublingually, subcutaneously and intravenously. All these methods expose healthy cells to the chemotherapy drug. Therefore, all of these methods of administration put the patient at risk for unwanted side effects and recurrence of the cancer. Thus, there is a need for a method of treatment for cancers and tumors that is affordable, effective, without side effects and predictable.

There is also a current need for a treatment that not only targets the cancer and tumor cells but also has the ability to eradicate the microorganisms in the specific site in order to prevent the cancer from recurring. There is no chemotherapy treatment on the market that targets both the cells and the microorganisms at the site.

THE SUMMARY OF THE INVENTION

The benefits of the various embodiments of the present invention are, in part, that its novel use and novel method of application described herein applies the novel treatment composition directly on the target site. The present invention provides a novel composition and a novel method for anti-cancer and anti-tumor treatment, which has the abilities of tissue dissolution, disinfection, tissue degradation, microbicidal action, bactericidal action, anti-fungal action, tissue removal and apoptosis. Also, embodiments of the present invention comprise a composition and method of use, whereby the composition is applied directly on the target site so it can kill the abnormal cells, infected cells and the microorganisms at the target site. Then, the by-products are rinsed away. The present invention can reach inoperable cancers and tumors by using needles, catheters, and other instruments to reach the target site.

Embodiments of the present invention utilize a proven and desired mode of attacking cancer and tumor cells by a method that has not been used before. Embodiments of the present invention use an action that kills cells, which is disrupting the disulfide bonds by a new method of application for a new use. The novel composition for cancer and tumor treatment is applied directly on the targeted cells and with predictable results for killing the targeted cells. Furthermore, since the composition is directly applied to the target site, harmful side effects associated with chemotherapy drugs are greatly reduced, since the composition does not travel via hematogenous route. Lastly, the novel composition is effective in killing the microorganisms in the target area which is very important to ridding the affected site area of not only the cancer and tumor cells, but also the microorganisms of the site that may have caused the cells to become cancerous.

The preventing and arresting of abnormally growing cells, cancer cells, tumor cells and cells infected with viruses are achieved by the disruption of the disulfide bond. Embodiments of the present invention use a chemical depilatory to break disulfide bonds for a new use and mode of application. There is a new group of anti-cancer and anti-tumor drugs that are antibody-drug linkers that focus their action on the disulfide bonds in the target cell. The newer anti-cancer and anti-tumor drugs interfere with the disulfide bonds to disrupt and prevent proper folding of proteins, and functioning of the cells. For example, new anti-cancer drugs use biodegradable spacers that target the disulfide bonds.

The present invention comprises a new use of and a new method of applying chemical depilatories that have been used for decades because of their ability to weaken hair by affecting disulfide bonds in the keratin in the hair, thus facilitating its removal from the skin. The disulfide bond is weaker than the C—C and C—H bonds in the keratin. Thus the disulfide bond is referred to as the weak link. U.S. Pat. No. 6,425,891 discloses removal of unwanted hair on the body by the use of a thioglycolate depilatory, which breaks the disulfide bonds in the keratin of the hair. The disulfide bonds are located between the cysteine groups in the keratin of the hair. Breaking the disulfide bonds in the hair allows the hair to be easily wiped away and removed. Therefore, disulfide bonds are found in all living cells, because the basic structure of cells requires disulfide bonds to be present.

The novel application of the present invention utilizes a known process of disrupting disulfide bonds for a new use in cells and tissues of cancers and tumors. Since cancer and tumor cells are normal cells that have lost its ability to self-regulate, they grow and function abnormally but still contain disulfide bonds. Disulfide bonds are found in secretory proteins, mRNA, red blood cells, white blood cells, hematopoeisis cells, fibronectin, blood vessels, immunoglobins, macrophages, neutrophils, lysosomal proteins, membrane proteins, antibodies, growth factors, insulin and exoplasmic domains of stability of proteins in extracellular tissue, which are still needed in cells that have abnormal growth.

Furthermore, in both normal and abnormal cells, disulfide bonds are also found in neurokeratin of the myelinated sensory nerve A fibers that can be found in the pulpal tissue. Disulfide bonds are needed for protein folding and the tertiary structure of proteins. Disulfide bond formation is in the endoplasmic reticulum. The soft tissue of the bone cavity contain hematopoeisis cells, red blood cells, white blood cells, blood vessels along with inflammatory cells and bacteria if infected which have disulfide bonds.

In addition, in both healthy and abnormal growth cells, DNA, RNA, or proteins are dependent upon the disulfide bonds for their integrity and existence. Also the endoplasmic reticulum contains disulfide bonds that are needed in order for the endoplasmic reticulum to function properly and allow protein folding. Therefore, once the disulfide bonds are broken, the endoplasmic reticulum and the cell lose their ability to function and fold proteins. This causes cellular breakdown.

Disulfide bonds are found in heparanase, which is overexpressed in tumor cells and is associated with the metastatic potential of tumor cells. Leukemia is an abnormal proliferation of white blood cells, which contain disulfide bonds.

An infected area having neoplastic cells needs to have its microorganism eradicated by embodiments of the present invention. By using the composition and method, the infected area of the human body may be treated by a chemical depilatory that can cause apoptosis in the microorganisms as well as in abnormal cells. Embodiments of the present invention comprise a composition applied to the infected area, which breaks disulfide bonds present in the microorganism or in the protein that the microorganism (a virus) needs in order to be vital. When the disulfide bonds are broken in the infected tissue, the cells' functions are disrupted. Disulfide bonds in bacteria are broken by the present invention as well as in the infected dysplastic tissue.

The preventing and arresting of abnormally growing cells, cancer cells, tumor cells and cells infected with viruses are achieved with the disruption of the disulfide bond by the present invention's novel application of the novel compositions, Embodiments of the present invention use a chemical depilatory to break disulfide bonds in cancer cells, tumor cells, and microorganisms. Human papillomavirus (HPV) according to the Centers for Disease Control and Prevention (CDC) can cause cervical cancer and other types of genital cancers HPV (a virus and a microbe) has disulfide bonds within it The headings used herein are for organizational purposes only and are not meant to be used to limit the scope of the description or the claims. As used throughout this application, the word "may" is used in a permissive sense (i.e., meaning "having the potential to"), rather than the mandatory sense (i.e., meaning "must"). Similarly, the words "include," "including," and "includes" mean including but not limited to.

In some of the present invention's embodiments sodium hypochlorite and calcium hydroxide are utilized for their tissue dissolving ability. For example, sodium hypochlorite is a widely used tissue dissolving agent. Sodium hypochlorite's effectiveness is dependent on its concentration and irrigation time and is highly effective at 5.25% for 40 minutes and ineffective at 1.3-2.5%. Calcium hydroxide paste is used for its alkaline property as specific limitations. Both, however, sodium hypochlorite and calcium hydroxide do not have the ability to eradicate all the bacteria. Sodium hypochlorite and calcium hydroxide need to be in direct contact to be effective. Sodium hypochlorite can dissolve organic tissue, but cannot predictably inactivate endotoxins. Sodium hypochlorite is not effective against bacteria, such as *Enterococcus faelicalis*. Calcium hydroxide has some antibacterial effect, but is also ineffective against *Enteroccucs faecali*.

The novel method of the present invention can disrupt the functioning of tissues contain disulfide bonds that are derived by coupling of two thiol groups by means of a chemical depilatory to benefit the patient. The linkage is called as an S—S bond or disulphide bridge. When the disulfide bonds are broken, cell death or apoptosis occurs. Apoptosis is needed to kill cancer, tumor and bacteria. Disulfide bonds are present in bacteria because they serve a protective role for the bacteria. Further, in humans also, disulfide bonds are found in secretory proteins, lysosomal proteins, and exoplasmic domains of stability of proteins in extracellular tissue. Further, disulfide bonds are also found in neurokeratin of the myelinated sensory nerve A fibers. When disulfide bonds are broken in abnormally growing tissues including cancer and tumor cells, apoptosis occurs, which eradicates cancer and/or tumor cells from the body.

The composition includes calcium hydroxide, sodium hydroxide, and potassium thioglycolate, so that the composition controls and eliminates tissues affected by abnormal growth. Tissues with bacterial infections may lead to cancer. The present invention's novel use of a depilatory's keratin-degrading ability to disrupt or break the disulfide bond in order to interfere with cells' ability to function, survive, and perpetuate in cancer tissue, infected tissue and tissue with abnormal growth. The present invention uses a depilatory composition (a composition that degrades, denatures, weakens and cleaves hair in order to remove it from outside of the body) for new uses and applications in oral medicine, dentistry, and medicine.

The present invention further provides a novel method and composition for dissolving disinfecting, degrading, and removing tissue from the body and a specific site in tissue within a bony cavity. The novel method of use of the present invention includes but not limited to dissolving, degrading, and removing tissue, and disinfecting, lubricating, deodorizing with a composition comprising calcium hydroxide, sodium hydroxide, potassium thioglycolate, water, mineral oil, urea, cetearyl alcohol, and ceteth-20, lanolin, aloe, fragrance, so that the composition combines many needed functions and applications into one medicament that can be used for therapies on all tissue types including abnormal, inflamed, normal, and infected tissues. The present invention's novel method of breaking of disulfide bonds in infected tissue and tissue with abnormal growth disrupts cells' ability to survive causing apoptosis or cell death like it does in bacteria, yeast, and microorganisms.

The present invention further provide a novel composition of matter for use in tissue dissolution, tissue degradation, disinfection, deodorizing, bactericidal treatments, anti-fungal treatments, lubrication, and removing abnormally growing tissue in a specific site in a hard bony cavity. The present invention combines the irrigants and antimicrobial agents into one composition for its use in chemotherapy for cell death. The novel composition of matter includes calcium hydroxide, sodium hydroxide, potassium thioglycolate, water, mineral oil, urea, cetearyl alcohol, and ceteth-20, for use as an anti-cancer and/or anti-tumor drug that degrades inflamed tissues and tissue having abnormal growth as seen in neoplasms and in tissues infected with microorganisms.

Further, the novel use according to the present invention has a number of advantages. First, the present invention provides a novel depilatory composition and a novel method for cancer treatments. The present invention utilizes the ability of the chemical depilatory to break disulfide bonds in the abnormal growth tissues, soft tissues and, connective tissues within the body. By breaking the disulfide bonds, the chemical depilatory weakens the structure of the infected dysplastic tissue. Further, the present invention provides a composition that provides effective and rapid results as shown by experimental results regarding apoptosis of bacteria obtain by the inventors. The chemical depilatories work at a fast rate of within five minutes. The chemical depilatory's ability to be effective within minutes of its application provides an advantage in patient care since the operating time can be kept to a minimum. Furthermore, the composition and the method are capable of removing debris that is formed during a cancer treatment. Furthermore, the present invention provides a composition that is also capable of cleaning hard bones surfaces to ensure that the surfaces are cancer-free.

Further, the novel method of the present invention simultaneously integrates many processes in order to be effective. The novel method of the present invention makes new use of a chemical depilatory in medicine in order to facilitate the removal of abnormal tissue and associated bacteria and microorganisms. The novel use of the chemical depilatory facilitates removal of material within the bony system as it lubricates, irrigates, disinfects, dissolves, cleanses, deodorizes and removes the smear layer. Furthermore, the chemical depilatory has antimicrobial benefits. The novel method of the present invention utilizes the chemical depilatory as a single irrigant that combines tissue dissolving ability and smear layer removal capacity with antibacterial properties. Furthermore, the present invention facilitates breaking glycosaminoglycans (GAG) bonds within the smear layer and thus facilitates its removal. Also, the novel use of the present invention utilizes the chemical depilatory's ability to break disulfide bonds present in proteins, deoxyribonucleic acid (DNA), ribonucleic acid (RNA), neoplastic and pulpal cells disrupt the cell's ability to function. Furthermore, the novel method of the present invention dislodges pulpal calcification by breaking the bonds in the tissue surrounding it. Next, the present invention novel method and use dissolves, removes and degrades tissues within the body that has abnormal growth as in neoplasms, granulomas and/or infected tissues that contain bacteria, fungi (yeast), and microorganisms.

Further, the present invention in a novel method utilizes a chemical depilatory for removal tissue from a specific soft tissue site and within a hard bony cavity. The present invention utilizes a chemical depilatory in a novel method and application and use for removing a soft tissue, necrotic tissue, debris, infected and abnormal tissue from the targeted site including within the hard tissue cavity. Further, the present invention provides a composition that is effective on mineralized surfaces. Furthermore, the composition provided by the present invention is useful in medicine, especially at inoperable sites, in long bones and in preparing sites for scaffolding of new cells for regeneration after the cancerous and tumorous and abnormal cells are removed.

These and other advantages will be made more apparent from the disclosure of the present invention contained herein.

The preceding is a simplified summary of the present invention to provide an understanding of some aspects of the present invention. This summary is neither an extensive nor exhaustive overview of the present invention and its various embodiments. It is intended neither to identify key or critical elements of the present invention nor to delineate the scope of the present invention, but instead to present selected concepts of the present invention in a simplified form as an introduction to the more detailed description presented below. As will be appreciated, other embodiments of the present invention are possible, utilizing, alone or in combination, one or more of the features set forth above or described in detail below.

THE BRIEF DESCRIPTION OF THE DRAWING

The above and still further features and advantages of the present invention will become apparent upon consideration of the following detailed description of embodiments thereof, especially when taken in conjunction with the accompanying drawings, and wherein.

Figure 1:
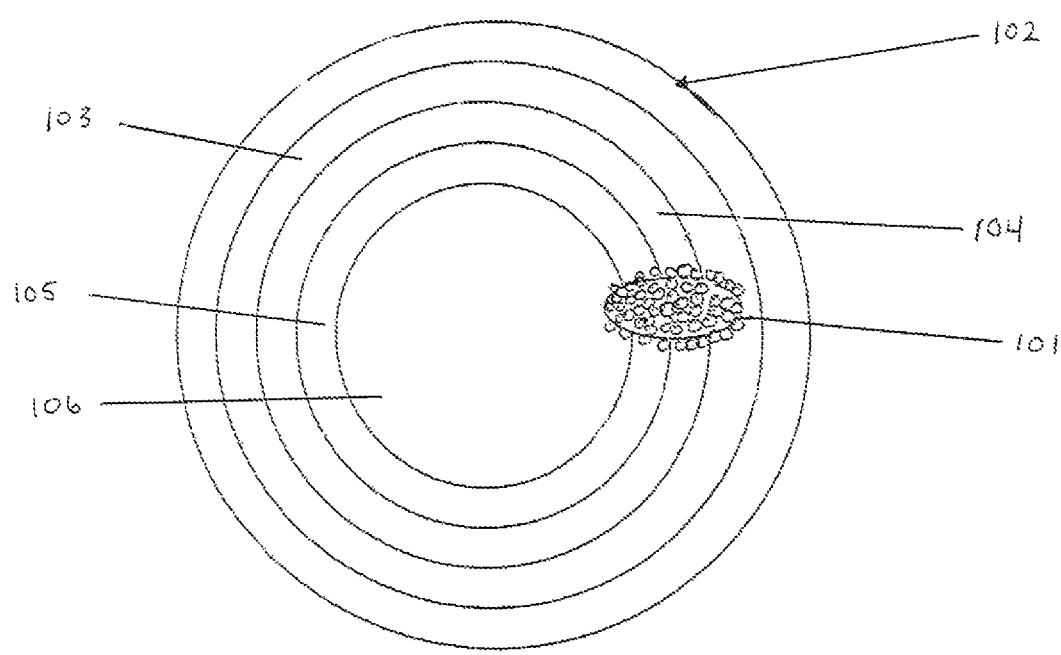
FIG. 1 is an example of dysplastic cells/tissues from the cross-section of the colon.

The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include," "including," and "includes" mean including but not limited to. To facilitate understanding, like reference numerals have been used, where possible, to designate like elements common to the figures.

THE DETAILED DESCRIPTION OF THE INVENTION

The present invention will be illustrated below in conjunction with an exemplary application, e.g., root canal treatment. Although well suited for use with, e.g., a medical application having disulfide bonds and requiring breakage of disulfide bonds, the present invention is not limited to any particular type of medical application. Those skilled in the art will recognize the disclosed techniques may be used in any medical or non-medical application in which it is desirable to provide breakage of disulfide bonds.

The phrases "at least one", "one or more", and "and/or" are open-ended expressions that are both conjunctive and disjunctive in operation. For example, each of the expressions "at least one of A, B and C". "at least one of A, B, or C", "one or more of A, B, and C", "one or more of A, B, or C" and "A, B, and/or C" means A alone, B alone, C alone, A and B together, A and C together, B and C together, or A, B and C together.

The term "a" or "an" entity refers to one or more of that entity. As such, the terms "a" (or "an"), "one or more" and "at least one" can be used interchangeably herein. It is also to be noted the terms "comprising", "including", and "having" can be used interchangeably.

The term "automatic" and variations thereof, as used herein, refers to any process or operation done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material."

The terms "determine", "calculate" and "compute," and variations thereof, as used herein, are used interchangeably and include any type of methodology, process, mathematical operation, or technique.

In the following detailed description, numerous specific details are set forth in order to provide a thorough understanding of embodiments or other examples described herein. In some instances, well-known methods, procedures, compositions, or components have not been described in detail, so as to not obscure the following description. Furthermore, the examples disclosed are for exemplary purposes only and other examples may be employed in lieu of, or in combination with, the examples disclosed. It should also be noted the examples presented herein should not be construed as limiting of the scope of embodiments of the present invention, as other equally effective examples are possible and likely.

FIG. 1 shows a cross-sectional view of a colon 100 in accordance with an embodiment of the present invention. The colon 100 includes dysplastic tissue 101, as shown in the figure. Because of the abnormal tissue with possible microbes within it 101, the colon 100 is under treatment. The colon 100 includes the following layers: serosa 102, muscle 103, submucosa 104, mucosa 105. The lumen 106 is the inner cavity. The purpose of the present treatment is to completely remove the dysplastic tissue 101 (as it is infected or injured, and can infect surrounding healthy tissue), and that includes removal of all tissues, debris and microorganisms from targeted site.

Tissues of the dysplastic tissue 101 can contain microorganisms which also must be killed and removed. Microorganisms have been known to cause cancer like Human papillomavirus (HPV) does. Therefore, the microorganisms in the target site must be removed along with the abnormal cell growth.

According to an embodiment of the present invention, all the tissues and microorganisms include disulfide bonds. The disulfide bond is a covalent bond that is derived by coupling of two thiol groups. The linkage is called an S—S bond or a disulfide bridge. The disulfide bonds are present in a plurality of living and non-living species. For example, disulfide bonds are present in bacteria and serve a protective role for the bacteria. Further, in humans also, disulfide bonds are found in secretory proteins, lysosomal proteins, and exoplasmic domains of stability of proteins in extracellar tissue. Further, disulfide bonds are also found in neurokeratin of the myelinated sensory nerve A fibers. Furthermore, disulfide bonds are present in HNGB1 (high-mobility group protein-1), which is a mediator of inflammation. According to an embodiment of the present invention, a method is provided for utilizing the disulfide bond or S—S bond for cleaning out the tissue 101 that has abnormal growth.

Tissues of the target site 101 include disulfide bonds. Disulfide bonds act like a glue and hold together molecules and proteins. If the disulfide bonds are broken, it may weaken and break down structure of the cells and tissues in site 101 and facilitate removal of cells and tissues from the site 101.

Figure 2:
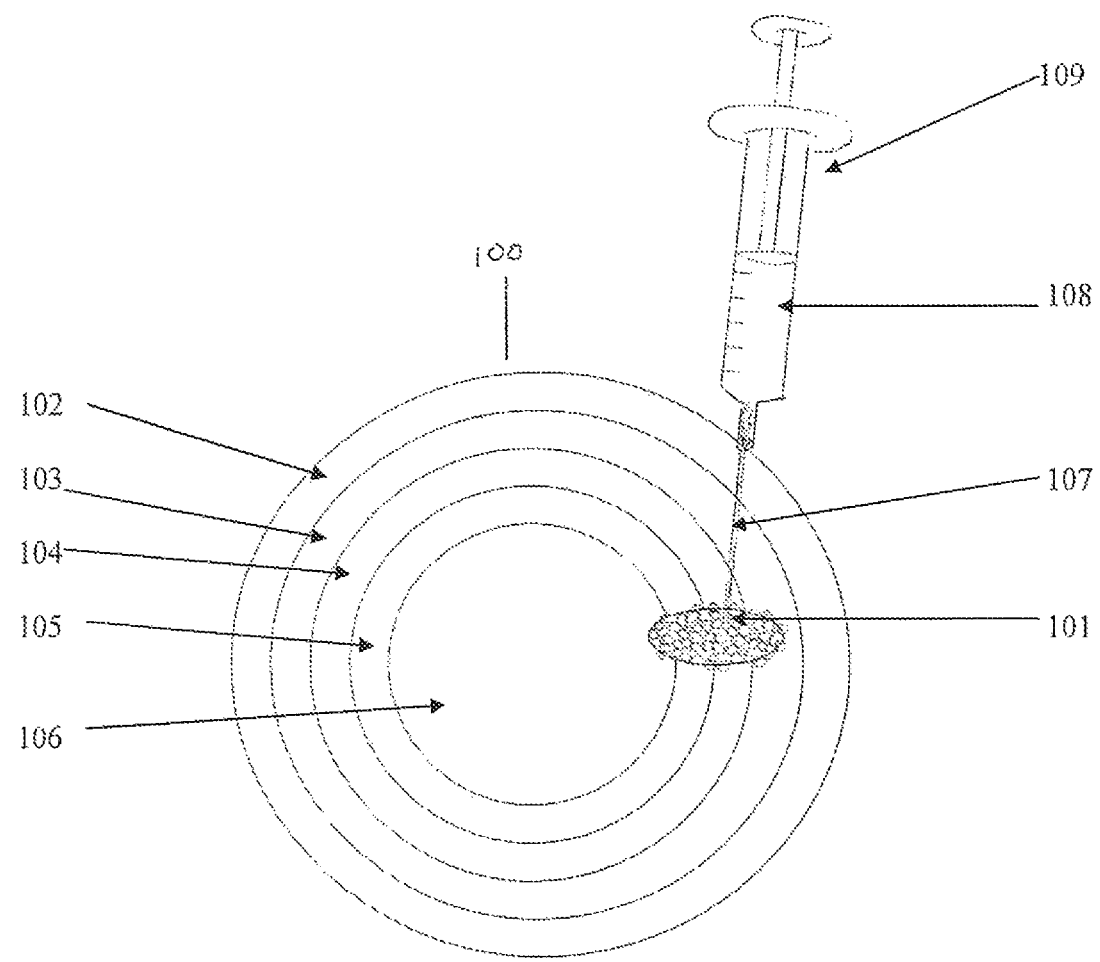
FIG. 2 illustrates the targeted site in FIG. 1 at a stage of treatment showing access to the targeted site in accordance with an embodiment of the present invention.

FIG. 2 depicts the colon 100, during the treatment, showing the syringe 109 containing the solution (an embodiment of the composition according to the present invention) 108 with a disposable needle 107 accessing the target area according to an embodiment of the method of the present invention. The tissue is accessed, as shown in the FIG. 2.

Figure 3:
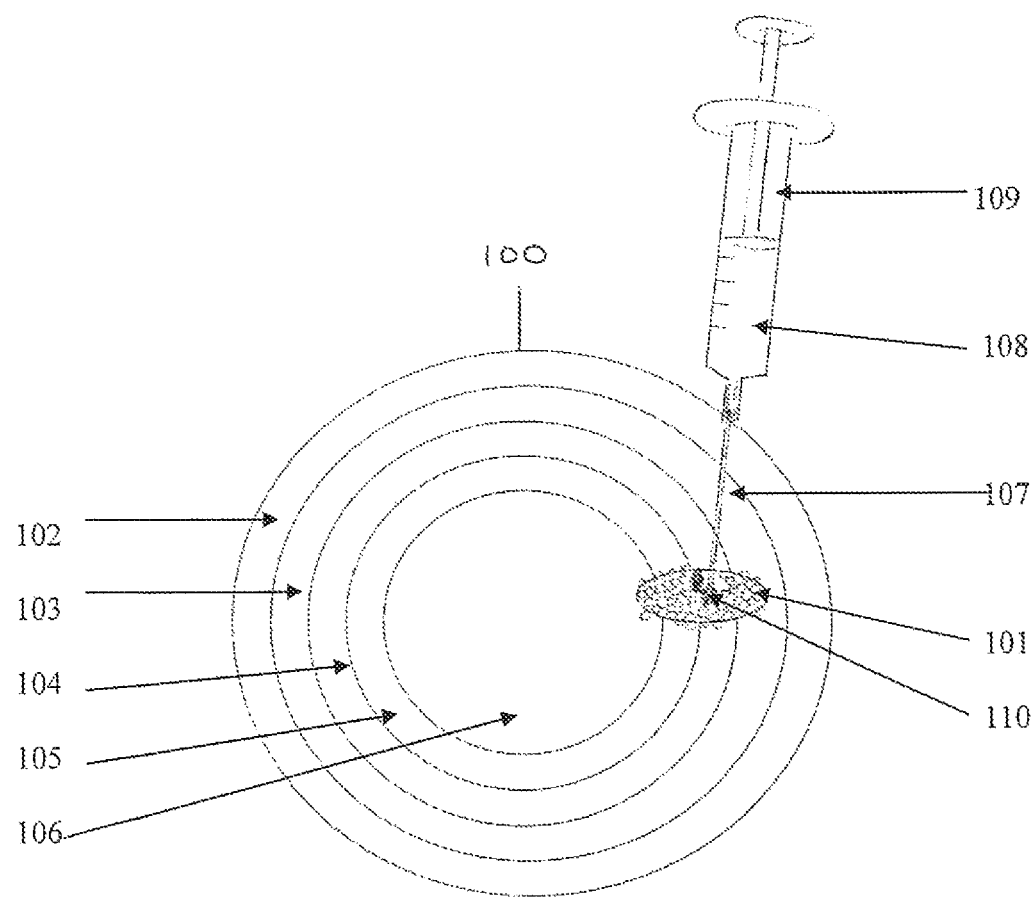
FIG. 3 illustrates the targeted site in FIG. 1 at a further stage of treatment showing a composition being applied in accordance with an embodiment of the present invention at the targeted site.

FIG. 3 depicts introduction of a few drops 110 of the treatment composition 108 into the target site 101 according to an embodiment of the method of the present invention. The composition 108 is delivered to the site 101 into a cavity using a disposable needle 107.

According to an embodiment of the present invention the composition 108 is a chemical depilatory. The present invention utilizes the chemical depilatory as a medicament for irrigation, disinfection, and lubrication to provide antimicrobial properties and further facilitate removal of the dysplastic tissue. In an embodiment of the present invention, the composition 108 breaks the disulfide bonds of the dysplastic tissue and microbes. The breakage of the disulfide bonds degrades structure of the abnormal tissue in order to remove infected tissue.

The chemical depilatories have been used for a wide variety of purposes. For example, chemical depilatories have been used for reducing microbial levels on the hide of an animal. Further, the chemical depilatories have been used to remove hair from skin and outer extremities such as the arms, legs, face, and underarms. Furthermore, the chemical depilatories have been used to remove unwanted hairs from the external skin of both animals and humans.

Furthermore, tissues of the muscles of the colon 103 and hair have the similar characteristic of containing disulfide bonds as both are derived from neural crest stem cells. The hair follicle bulge is derived from the cranial neural crest as are the muscles of the colon. Since chemical depilatories have been used on hair, the present invention utilizes the chemical depilatories in medical therapeutic applications.

According to an embodiment of the present invention, the composition 108 includes active ingredients of calcium hydroxide, sodium hydroxide, and potassium thioglycolate. In an embodiment of the present invention, the composition 108 further includes mineral oil, urea, cetearyl alcohol, and ceteth-20, which contribute to ability of the composition 108, 110 to produce desired results.

According to an embodiment of the present invention, the composition 108 is capable of weakening attached connective tissue as well as removing soft tissue from the cavity of a hard, bony tissue. In an embodiment of the present invention, the composition 108 provides a single irrigant composition that dissolves tissue, disrupts cell functioning, provides anti-microbial action, and has antibacterial capability.

Furthermore in an embodiment of the present invention, the composition 108 (or chemical depilatory) may be used by a medical professional in cavities for removing tissue and debris.

The composition 108 may perform multiple roles in the treatment method. For example, the composition 108 may act as an irrigant, disinfectant, chelation agent, conditioner, antimicrobial agent and lubricant for preparing the space, according to an embodiment of the present invention. The composition 108 includes calcium hydroxide, sodium hydroxide, and potassium thioglycolate in combination. Furthermore in a further embodiment of the present invention, the composition 108 may include mineral oil, urea, cetearyl alcohol, and ceteth-20 for irrigation, disinfection, lubrication, removing the smear layer, dissolving tissue and as an anti-bacterial agent.

In an embodiment of the present invention, the composition 110 may be used in medical usages in order to break disulfide bonds present in tissue, and to be effective against bacteria present in the pre-cancerous stage. The composition 110 may further provide for removal of soft tissue inside of a cavity. Further, according to an embodiment of the present invention, the composition 110 may provide preparation of regeneration and formation of mineralized and soft tissue in a cavity (e.g., a human or animal). Furthermore, the composition 110 may be used in medicine, for example, in long bones and in preparing skeletons for museums, etc.

Figure 4:
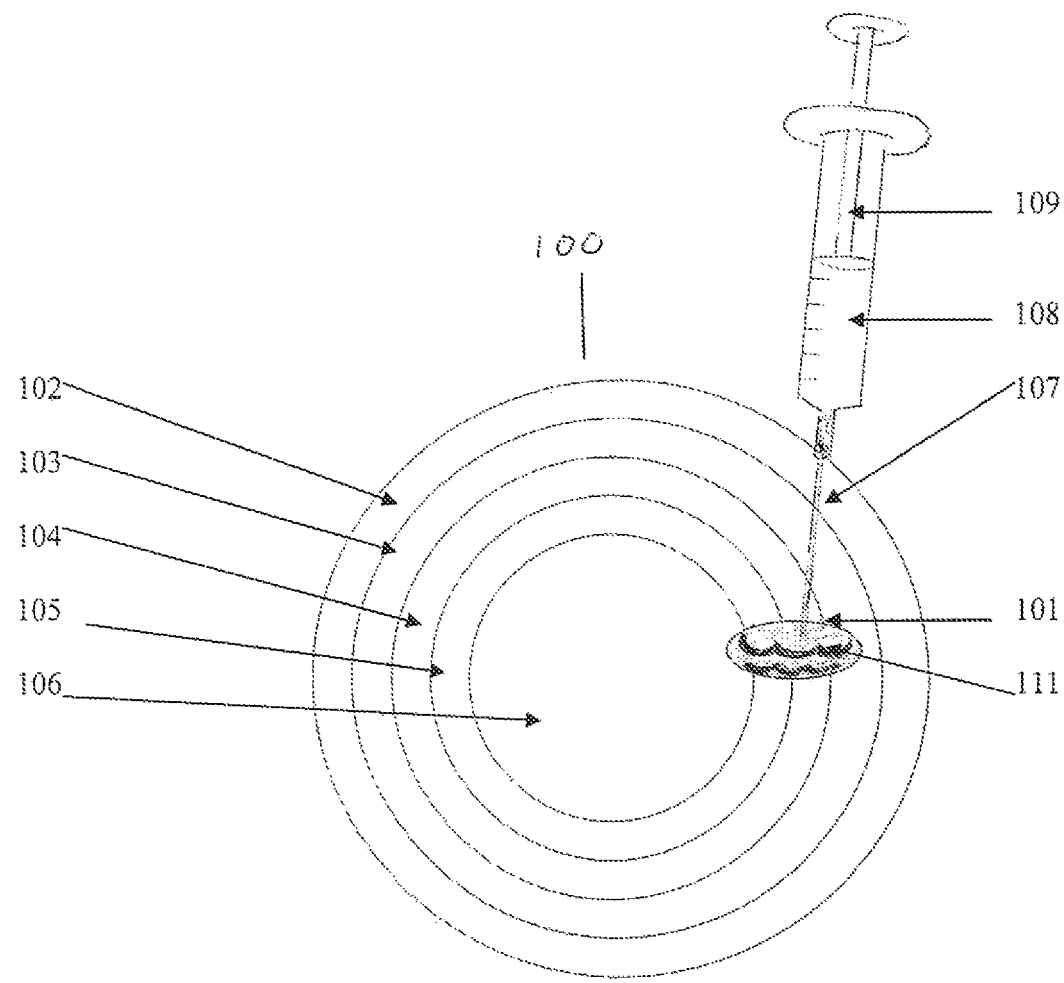
FIG. 4 illustrates the targeted site in FIG. 1 at a further stage of treatment showing a composition accessing the entire site in accordance with an embodiment of the present invention.

FIG. 4 depicts the composition 108 accessing the entire site 101 by saturating the target site with the present solution 111. The composition 108 provides removal of soft, connective tissue and from the soft tissue within a tissue cavity. In an embodiment of the present invention, the composition 108 is a chemical depilatory that removes soft tissue, necrotic tissue, debris, and calcified tissue from within the cavity.

According to an embodiment of the present invention, the composition 108 includes active ingredients comprising calcium hydroxide, sodium hydroxide, and potassium thioglycolate, as discussed above.

In one embodiment of the present invention, calcium hydroxide (present in the composition 108) creates an alkaline environment so that microbial pathogens are not able to survive. In a further embodiment of the present invention sodium hydroxide (which is a strong base) is used in tissue digestion by bleaching. Further the sodium hydroxide breaks down chemical bonds in tissue as bone if present remains.

Further, in an embodiment of the present invention, potassium thioglycolate (present in the composition 108) breaks down sulfur bonds present in protein in tissues. Potassium thioglycolate reacts with the cystine present in the protein. The reaction is as follows:

2HS—CH$_2$—COOH(thioglycolic acid)+R—S—S—R (cystine=disulfide bridge)----2R—SH+HOOC—CH$_2$—S—S—CH$_2$—COOH(dithiodiglycolic acid).

Further, in an embodiment of the present invention the composition 108 may include, but not limited to, one or more of the following constituents: water, mineral oil, urea, cetearyl alcohol, D & C yellow No. 8, chromium hydroxide, the *theobroma* cocoa seed butter, iron oxides, fragrances, and ceteareth-20. According to an embodiment of the present invention, the mineral oil may fill surface cracks. Those skilled in the art will appreciate that the surface cracks, if not filled, may harbor bacteria. Further, the mineral oil may act as a lubricant. Further, according to an embodiment of the present invention, the urea may retain moisture, prevent skin infections, and treat inflammatory conditions in the skin.

According to an embodiment of the present invention, the cetearyl alcohol may include a coconut oil. The cetearyl alcohol can emulsify with cetearrth-20 and enhances the viscosity of the lotion.

Figure 5:
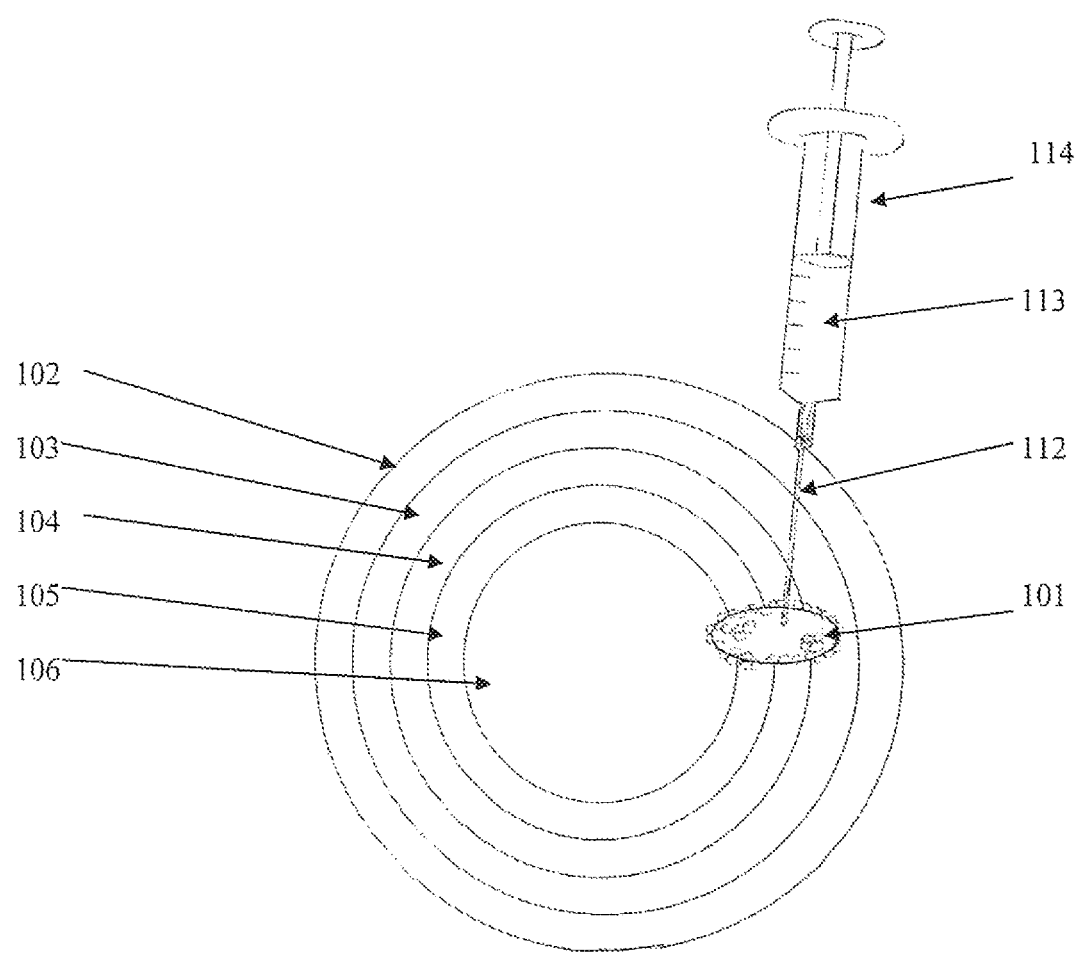
FIG. 5 illustrates the specific target site in FIG. 1 at a further stage of treatment showing an aspiration of the present solution of the end products and compositions and all tissues in the targeted area in accordance with an embodiment of the present invention.

Once the tissue has been cleaned out and the root canal area disinfected with help of the composition, a rinsing solution may be introduced, as shown in FIG. 5.

FIG. 5 shows the start of aspiration of the target site after treatment with the present solution (composition 108) using an aspirating disposable needle 112 that aspirates the dead cells and exudate 113 from within the target site 101 into the aspiration syringe 114.

Figure 6:
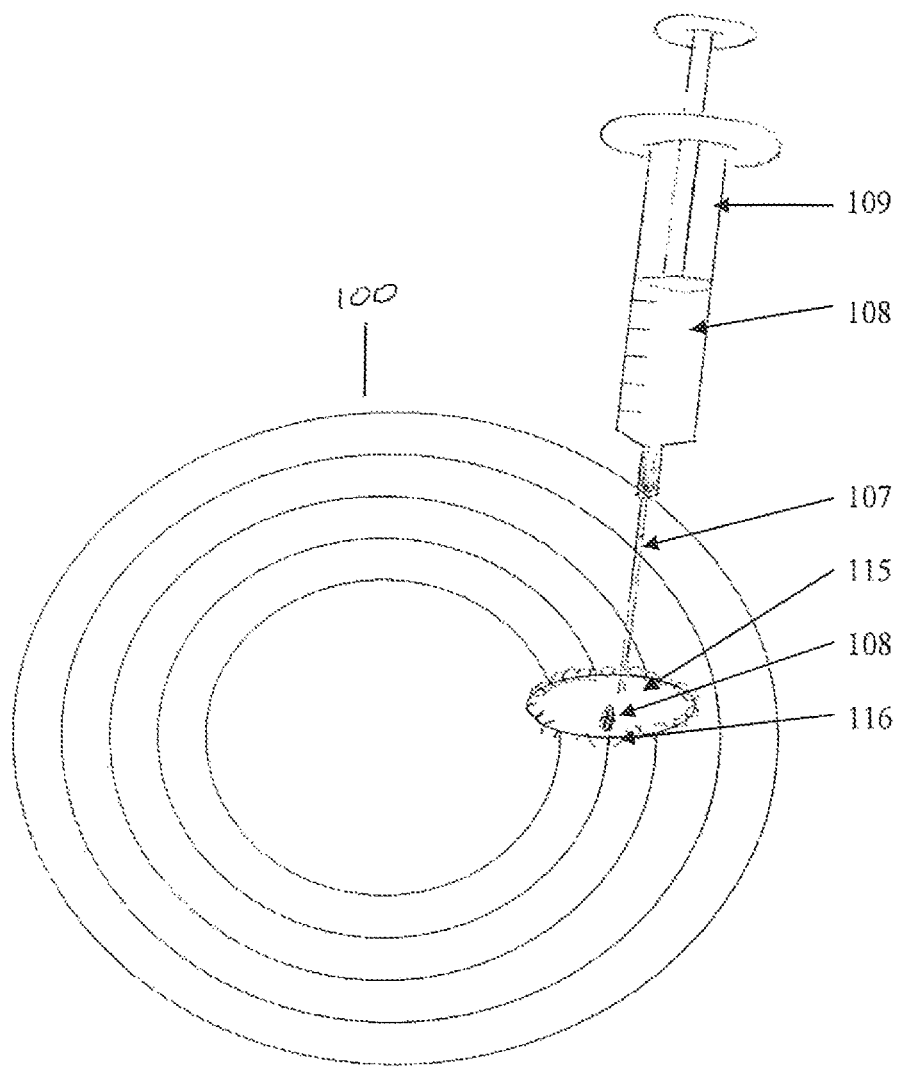
FIG. 6 illustrates the target site of FIG. 1 at a further stage of treatment showing the target site after aspiration and reapplying the present embodiments to the periphery of the cells/tissue and the border cells/tissue in accordance with an embodiment of the present invention.

FIG. 6 shows the colon 100 after aspirating the target site 115 and now the reapplying of the present solution 108 to the peripheral cells/border of the target area 116 with a disposable needle 107 from a syringe 109.

According to an embodiment of the present invention, the composition 108 (i.e., the chemical depilatory) breaks the disulfide bonds in the tissues. The breaking of bonds aids in the removal of unwanted tissue and debris. The composition 108 further lubricates, irrigates, disinfects, dissolves, cleanses and removes microbes. Further, the composition 108 (or the chemical depilatory) provides antimicrobial protection for the target area.

The composition 108 includes chemicals (that breaks the disulfide bonds, e.g., calcium hydroxide, sodium hydroxide, and potassium thioglycolate) with other substances (that are needed to lubricate, dissolve, disinfect and remove pulpal debris, e.g., mineral oil, urea, cetearyl alcohol and ceteth-20).

Furthermore the composition 108 provides cleansing and debriding of the target site area.

Hence the composition 108 provides disinfection, cleansing, irrigations and anti-microbial actions. Also, the composition 110 further may be used to remove the debris that is formed during treatment and dissolve proteins within the tissue area.

Furthermore according to embodiment of the present invention, the composition 108 may be used for cleaning, irrigating, disinfecting, etc. of inside of any cavity (e.g., a hard bony cavity). For example, the composition may be used for intra-medullary reaming and irrigating (e.g., to be used before a rod in orthopedics), maceration (e.g., cleaning animal skulls & bones used of preserving them), preparing a bony surface for stem cells, for regeneration of new tissue, and for formation of mineralized tissue.

In addition, the composition 108 may be used for preparing a bony surface for cellular differentiation, tissue formation, and tissue regeneration. Those skilled in the art will appreciate that for making regeneration of stem cells successful, the diseased or unwanted cells must be removed, because they damage the underlying tissues' ability to generate new cells on its own. In an embodiment of the present invention, the composition 110 removes the diseased or unwanted or infected cells, and provides a clean area for regeneration of stem cells.

Moreover the composition 108 may assist a dentist to use the dental stem cells after cleansing the target area with the aid composition. The stem cells may be used within the pulpal chamber. For example, an embodiment of the present invention provides a root canal therapy, whereby a root canal procedure will be cleaning the chamber/roots and then placing stem cells to re-grow pulpal, dentinal and mineralized tissue. The composition 108 provides a clean surface for placement of stem cells.

Figure 7:
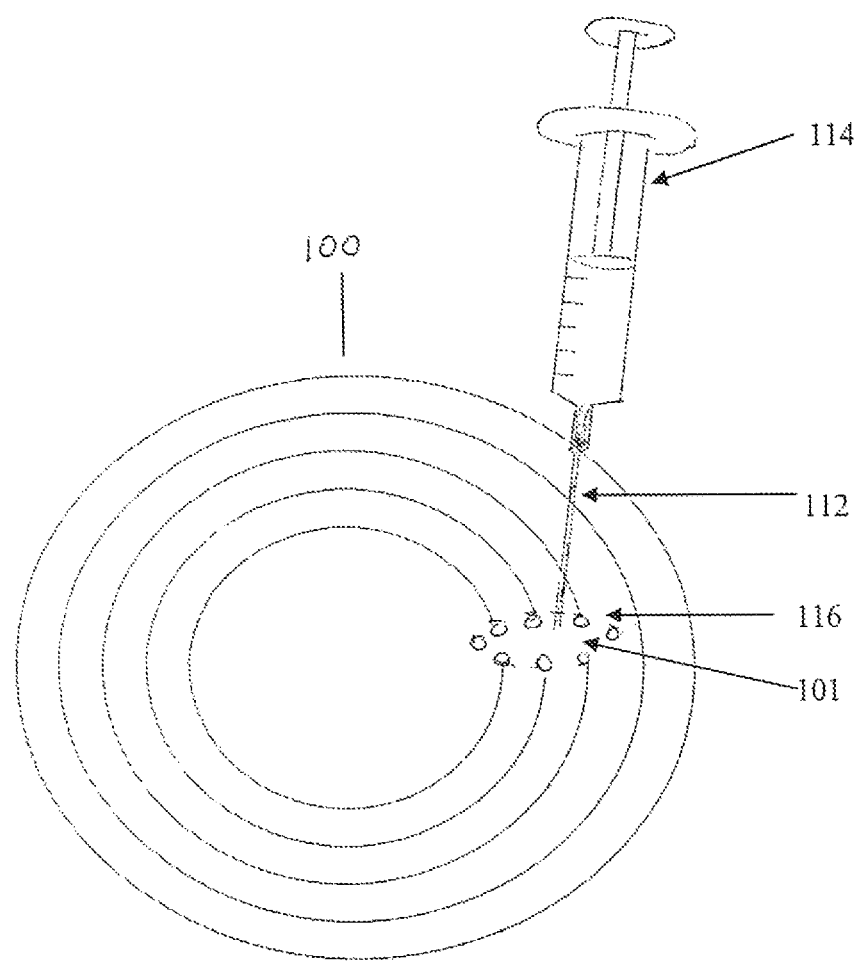
FIG. 7 illustrates the targeted site of FIG. 1 at a further stage of treatment showing the target site periphery cells/tissue and border cells/tissue and end products and composition being aspirated in accordance with an embodiment of the present invention.

FIG. 7 shows introduction of aspirating of the target site's peripheral cells 116 after treatment with the present solution using an aspirating disposable needle 112 that aspirates the dead cells and exudate from within the target site 113 and peripheral cells 116 into the aspiration syringe 114.

Figure 8:
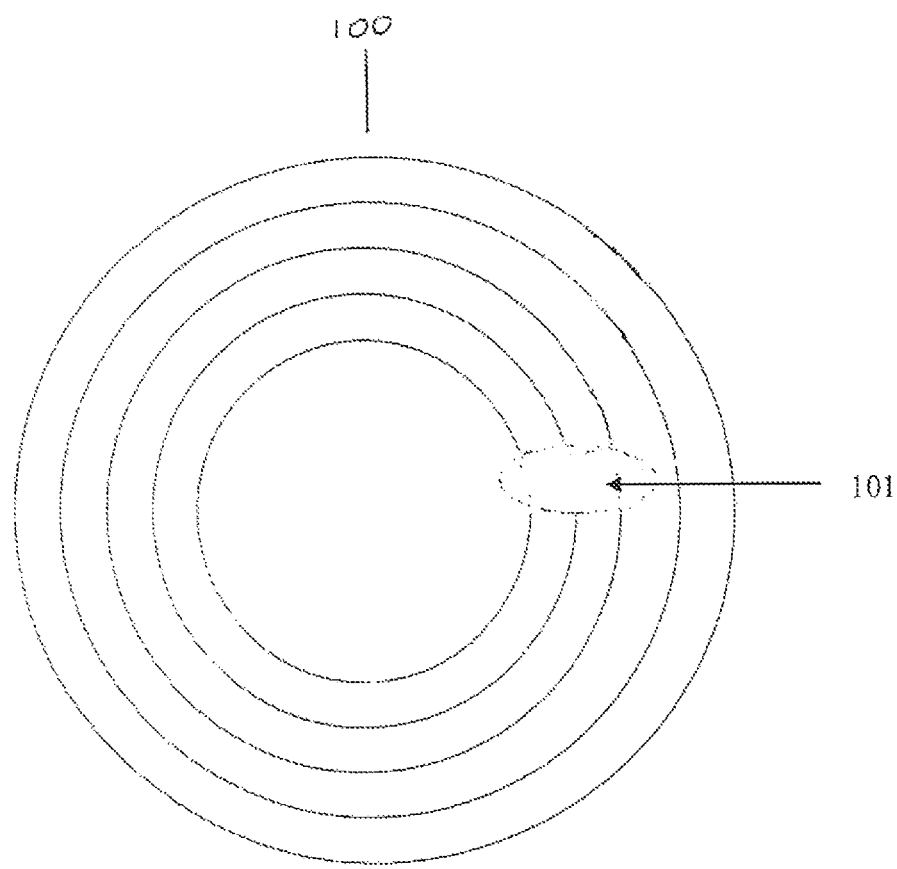
FIG. 8 illustrates the targeted site of FIG. 1 at a further stage of treatment showing the target site periphery cells/tissue and border cells/tissue after aspiration in accordance with an embodiment of the present invention, thus being free from containing infected and dysplastic cells and tissues.

FIG. 8 shows the target site 101 free of dysplastic cells including all microorganisms that may have been within the target area.

Figure 9:
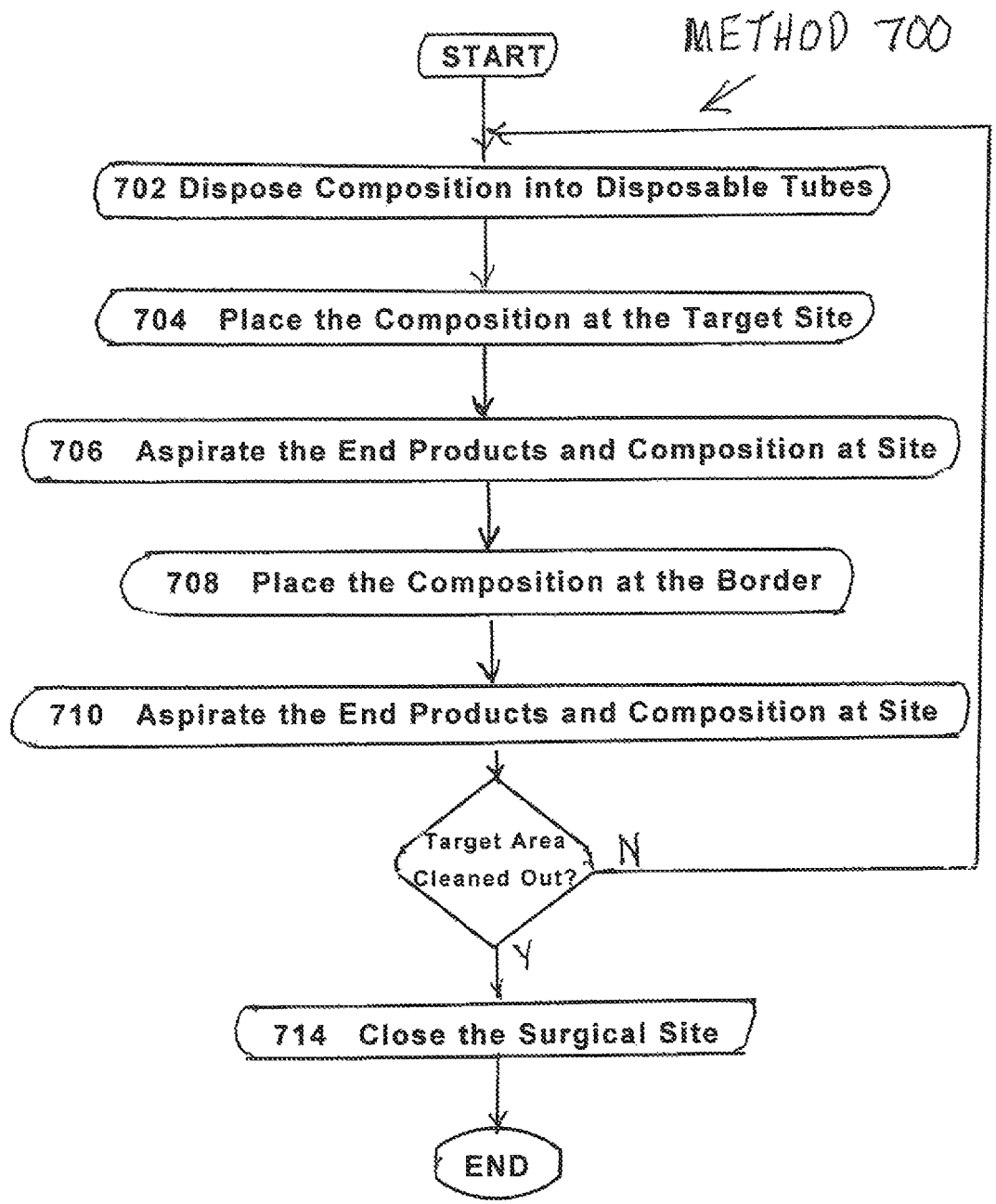
FIG. 9 is a flow chart of the method of treatment using a composition in accordance with an embodiment of the present invention.

FIG. 9 is a flowchart of a method 700 for treatment sites for anti-cancer, anti-tumor and areas with abnormal growth with/without microbes present, according to an embodiment of the present invention. According to an embodiment of the present invention, the method 700 provides using a chemical depilatory as a composition in endodontic. The method 700 is effective due to disulfide bonds presence in pulpal tissue of tooth.

At step 702, a chemical depilatory composition is dispensed into disposal tubes. Disposal needles may be attached to the disposable tubes. According to an embodiment of the present invention, the composition may include calcium hydroxide, sodium hydroxide, and potassium thioglycolate. In one embodiment of the present invention, calcium hydroxide (present in the composition) creates an alkaline environment so that endodontic pathogens are not able to survive.

In a further embodiment of the present invention sodium hydroxide (which is a strong base) is used in tissue digestion by bleaching. The sodium hydroxide breaks down chemical bonds and potassium thioglycolate (present in the composition) breaks down sulfur bonds present in protein.

In another embodiment of the present invention, the composition may further include mineral oil, urea, cetearyl alcohol, D&C yellow No, 8, chromium hydroxide, *theobroma* cocoa seed butter, iron oxides, fragrances, and ceteareth-20 to enhance its functioning, in addition to calcium hydroxide, sodium hydroxide, and potassium thioglycolate. According to an embodiment of the present invention, the mineral oil may fill surface cracks. Further, the mineral oil may act as a lubricant. Further, according to an embodiment of the present invention, the urea nay retain moisture, prevent skin infections, and treat inflammatory conditions in the skin. Further, according to an embodiment of the present invention, the cetearyl alcohol can emulsify with cetearyl alcohol can emulsify with ceteareth-20 and enhances viscosity of the lotion. In an embodiment, the cetearyl alcohol ay include a coconut oil.

At step 704, a few drops of the composition are placed at the target site with the disposable needle. At step 704, the composition or solution is placed at the target area until the targeted area is saturated with the composition. The solution is left there for about 1-3 minutes and up to 15 minutes determined by the medical professional.

At step 706, the composition or solution and its end products and other debris and microorganism at the targeted area are aspirated away from the targeted area by an aspirating needle.

At step 708, since there may be some dysplastic tissues remaining or infection/infected tissue remaining on the periphery of the area, repeat the method of application at the determined length of time on or about up to 15 minutes as recommended by the medical professional. Then aspirate with step 710. Repeating steps 708 and steps 710 as needed.

FIG. 8 also shows disulfide bonds in proteins according to an embodiment of the present invention. Disulfide bonds present in tissue proteins of a human body may be considered as a framework for living cells. In an embodiment of the present invention, in a human body, let say, an infected area having neoplastic cells is present. By using the composition of the present invention, the infected area of the human body may be treated successfully by the chemical depilatory causing apotheosis of the abnormal growing cells. In an embodiment of the present invention, the composition may be carefully applied to the infected area to break the disulfide bonds present in the infected area. When the disulfide bonds are destroyed in the infected area, a doctor will prevent regeneration of the neoplastic cells in that area. Further, DNA, RNA or proteins are dependent upon the disulfide bonds for their integrity and existence. Therefore, once the disulfide bonds are destroyed, the ability of that infected or abnormal cell to regenerate ceases.

Test Results

Test results will now be provided here to illustrate the above principles. The following example illustrates the operation of the present invention in accordance with an embodiment of the present invention. A person of ordinary skill in the art will appreciate the present invention may be performed for any medical use and is not limited to any particular medical application.

Testing of the present invention's anti-microbial activity was done in an independent laboratory in accordance with the USFDA Regulations 21 CFR Part 58. The testing of the present invention was done under the supervision of a quality assurance supervisor and a study director. The study was done at an off-site laboratory that performed the tests under protocol that includes reproducibility of test results and details to allow for inspection. The laboratory keeps all the documentation and details on file.

The testing of the test organisms were done with contact time of 5 minutes, 15 minutes, and 30 minutes. The time intervals were chosen so as to correspond to times that practitioners use in clinical practice. The maximum time was chosen as 30 minutes, since actual treatment time is approximately equal to 30 minutes. The testing of the test organism was done with contact time of 5 minutes, 15 minutes and 30 minutes. The time intervals were chosen so as to correspond to times that practitioners use in clinical practice in treatments done in a medical office, during an operation, and an out-patient procedure. The maximum time was chosen as 30 minutes, since the actual treatment time is approximately equal to 30 minutes. A maximum of 30 minutes is reasonable for an operating procedure. Recovery times were tested for bacteria using 2-5 days times and C. albicans with 2-5 days intervals. Recovery values are the colonies forming abilities.

The plate counts are based on colony formation units (CFU)/plate for both bacteria and yeast. For bacteria and yeast, the 25-250 CFU/plate is in a statistically accurate range. For mold, 8-80 CFU/plate is in a statistically accurate range. Soybean Casein Digest Agar was used as the medium for plates of the test organism of S. mutans and E.faecalis. Sabouraud Dextrose Agar was used for C. albicans. All plates were handled under laboratory conditions with their controls.

The test micro-organisms (i.e., E. faecalis, C. albicans, and S. mutans) were picked, because they are the prevalent organisms in inflammatory infections that are directly associated with cancer, tumors and creating an environment that is conducive for formation of dysplasic cells. Candida albicans, Streptococcus mutans and Enterococci faecalis are the microorganisms that have a major presence in the inflammatory lesion associated with cancer, dysplastic and tumor cells. Therefore, not only do the abnormal cells need to be eradicated, but also the micro-organisms at the target site.

Candida albicans are typically opportunistic infections in humans. Candida albicans are yeasts, a type of fungi, which are the causative agent for infections of candidiasis. Candida can create an environment that can trigger normal cells to become cancerous. Also, "Cancer cells were mixed with candida at a ratio of 1:10" and "A high attachment of candida to cancer cells (29-39%)"have been found in medical research. See Phagocytosis of Candida albicans by metastatic and non metastatic human breast cancer cell lines in vitro, Ghoneum M. Gollapudi S. Cancer Detect Prev. 2004; 28(1):17-26. Therefore, the composition needed for cancer treatment needs to kill both Candida albicans and the cancer cell, which the present invention does. Present medical research confirms that, when the disulfide bridge is disrupted in the target cell, the cell ceases to function. Our tests confirm that the test not only breaks the disulfide bond but also has the ability to kill Candida albicans, a fungi. Therefore, Candida is used as a test organism for it is important that the novel composition can kill both the Candida albicans present in the cancer tissue so that the site area is completely free from cancer and microorganisms that have the potential of being a precursor to cancer.

Streptococcus mutans is a gram-positive bacteria, which is cariogenic, produces acid, and furthermore, S. mutans has the ability to survive levels of oxygen tension and absence of essential nutrients. S. mutans can maintain microbial growth and continue acid production at low pH values. Therefore, it is an alpha-hemolytic Streptococcus species that has the ability to oxidize iron within red blood cells. Like S.mutans, S. bovis can cause endocarditis and may be blood-borne. S. bovis like S. mutans has the similar quality of "'Disulfide bonds are important for the stability of many extracellular proteins, including bacterial virulence factors" Functional analysis of paraloqous thiol-disulfide oxidoreductases in Streptococcus qordonii, Lauren Davey, Crystal K W Ng, Scott A Halperin, Song F Lee (J Biol Chem., 2013 Jun. 7; 288(23):16416-29; doi: 10.1074/jbc. M113.464578. Epub 2013 Apr. 24!). It is known that the gram-positive bacterium Streptococcus bovis has been associated with colon cancer for many years. Profiling the humoral immune response in colon cancer patients: Diagnostic antiqens from Streptococcus bovis, Harold Tialsma Marie Schuller-Guinard Edwin Lasonder Theo J. Ruers Hans L. Willems Dorine W. Swinkels (Int. J. Cancer: 119, 2127-2135 (2006). Also, S. mutans can cause ulcerative colitis, which can then lead to colon cancer. The ability to be able to eradicate Streptococcus bacteria from the target area is imperative for treatment of dysplastic tissue sites.

Enterococci faecalis, a bacteria, is found most commonly in persistent infections of the gut that lead to colon cancer. Due to the prevalence of E. faecalis in persistent gut infections that lead to cancer, it is essential to eliminate the targeted cancer site and to kill the bacteria at that site. E. faecalis oxidants are important, because they cause chromosomal instability (CIN) associated with sporadic adenomatous polyps and colorectal cancer (Carcinogenesis, 2002 Mar.; 23(3):529-36 teaches that Enterococcus faecalis produces extracellular superoxide and hydrogen peroxide that damages colonic epithelial cell DNA, Huycke M M, Abrams V, Moore D R). E. faecalis present at the target site must be eradicated from the target site, so that those microoganisms that have the ability to produce the oxidants strong enough to have cariogenic abilities are eliminated to prevent recurrence of the cancerous and tumorous growth.

The test microorganisms (i.e., E. faecalis, C. albicans, and S. mutans) were picked because they are the prevalent organisms in endodontic infections. Endodontic infections are mixed microorganisms or flora. Candida albicans, Streptococcus mutans and Enterococci faecalis are the microorganisms that have a major presence in the endodontic lesion, which all need to be eradicated. *Candida albicans* is typically an opportunistic infection in humans. *Candida albicans* are yeasts, a type of fungi that are in infections of root canals and cause oral candidiasis and are prevalent in HIV cases. The treatment of candidiasis is by the use of antifungal treatment and not by antibiotics. *Streptococcus mutans*, bacteria, have a large presence in dental caries and has the ability to dematerialize enamel by its ability to reach the critical pH that is needed. Furthermore, *S. mutans* has a significant presence in root canal infections, since it has the ability to survive levels of oxygen tension and absence of essential nutrients. *S. mutans* can maintain microbial growth and continue acid production at low pH values. *Enterococcus faecalis* bacteria is found most commonly in persistent radiographic lesions after root canal treatment. Due to the prevalence of *E. faecalis* in persistent endodontic infections, it is essential that the main persistent etiologic agent is eradicated during root canal instrumentation. Therefore, complete removal of irritants from the root canal system is best and most effective way to eradicate root canal infections.

The test results are obtained from a procedure for evaluation of products for anti-microbial activity against selected organisms at representative contact times. Products are peroxides that damage colonic epithelial cell DNA evaluated in a liquid matrix. The test organisms and contact times are chosen by sponsor. This is a quantitative test that allows the determination of the amount of organism reduction at predetermined intervals. All test method acceptance criteria were met. The acceptance criteria were that negative controls should be negative for growth, positive controls should be positive for growth, and neutralization should be confirmed at ~70%. Specific criteria for pass/fail of the test article must be determined by the sponsor.

Inoculum Preparation:

Plates of Soybean Casein Digest Agar (SCDA) media were inoculated with stock cultures of the test organisms *S. mutans* and *E. faecalis* and incubated at 30-35° C. for 18-48 hours. Plates of Sabouraud Dextrose Agar (SDEX) media were inoculated with stock cultures of the test organism *C. albicans* and incubated at 20-25° C. for 44-52 hours. Growth was harvested from the surface using a sterile bent glass rod and physiological saline solution 0.9% (PHSS).

Where necessary, culture suspensions were adjusted for the test procedure with PHSS to approximately ~108 CFU/ml using visual turbidity.

Test Article Preparation:

Test articles were prepared according to the product label or sponsor instructions and were tested without any additional manipulation or dilution.

Neutralization:

A 0.1 ml aliquot of the test article was mixed with 9.9 ml Dey-Engley Neutralizer Broth (DEYE). An additional tube of 10 mL of DEYE was prepared as a titer control. The tubes were inoculated with 0.1 ml of a test organism suspension diluted to approximately ≤10,000 CFU/mL, then mixed thoroughly. Aliquots from each tube were plated in triplicate onto SCDA and incubated at 30-35° C. for 2-5 days for *S. mutans* and *E. faecalis*. Aliquots from each tube were plated in triplicate onto SDEX and incubated at 20-25° C. for 2-5 days for *C. albicans*.

Controls:

Positive control tubes containing 10 mL PHSS were prepared. A 0.1 mL aliquot of the test organism was added to each tube. The positive control was assayed at 0 hour and the longest tested time point. The negative control consisted of plating sterile aliquots of applicable liquid media in triplicate and incubating as described in the test procedure.

Test Procedure:

Tubes containing 10 mL of each test article were prepared and inoculated with 0.1 mL of the test organism to yield ~106 CFU/mL. The test articles were mixed thoroughly.

At 5 minutes, 15 minutes and 30 minutes of exposure, 1.0 mL aliquots of the test suspension were removed and added to 9 mL of neutralizer and serially diluted to produce a 1:100 dilution of test suspension to neutralizer. The tubes were mixed thoroughly. Serial dilutions were made in the appropriate neutralizer and assayed using a standard spread plate method.

All plating was performed in triplicate. Bacterial test articles were plated onto SCDA and incubated at 30-35° C. for 2-5 days. Yeast test articles were plated onto SDEX and incubated at 20-25° C. for 2-5 days.

Quantitative analysis was used to study the anti-microbial activity of the present invention. The following formulas were used by the independent laboratory in preparing their report of the effectiveness of the present invention.

Calculations:

The log reduction values were calculated using the following formula:

$$\text{log reduction} = \log 10\ U - \log 10\ C,$$

wherein U=average positive control titer,

C=average recovered counts.

The percent reduction values were calculated using the following formula: % reduction=[1−1/10(log reduction)]×100

The percent neutralization is obtained according to the following equation: % neutralization=[(average sample count/plate)/(average control count/plate)]×100

Test Article—*Enterococcus faecalis*

| Identification | Exposure Intervals | Average Control Titer (CFU/ml) | Average Test Article Titer (CFU/ml) | Percent Reduction (%) | Log Reduction |
|---|---|---|---|---|---|
| Control | 30 minutes | 1.1 × 10 | 1.0 × 10 | 7 | 0.03 |
| | 5 minutes | | <2.0 × 10 | >99.9982 | >4.74 |
| Sample 1 | 15 minutes | 1.1 × 10 | <2.0 × 10 | >99.9982 | >4.74 |
| | 30 minutes | | <2.0 × 10 | >99.9982 | >4.74 |

Test Article—*Candida albicans*

| Identification | Exposure Intervals | Average Control Titer (CFU/ml) | Average Test Article Titer (CFU/ml) | Percent Reduction (%) | Log Reduction |
|---|---|---|---|---|---|
| Control | 30 minutes | 8.5 × 10 | 1.0 × 10 | −32 | −0.12 |
| | 5 minutes | | <2.0 × 10 | >99.9976 | >4.63 |
| Sample 1 | 15 minutes | 8.5 × 10 | <2.0 × 10 | >99.9976 | >4.63 |
| | 30 minutes | | <2.0 × 10 | >99.9976 | >4.63 |

Test Article—*Streptococcus mutans*

| Identification | Exposure Intervals | Average Control Titer (CFU/ml) | Average Test Article Titer (CFU/ml) | Percent Reduction (%) | Log Reduction |
|---|---|---|---|---|---|
| Control | 30 minutes | 4.1 × 10 | 4.5 × 10 | −11 | −0.05 |
|  | 5 minutes |  | <2.0 × 10 | >99.99951 | >5.31 |
| Sample 1 | 15 minutes | 4.1 × 10 | <2.0 × 10 | >99.99951 | >5.31 |
|  | 30 minutes |  | <2.0 × 10 | >99.99951 | >5.31 |

Neutralization

| Organism | Average control counts (CFU) | Average test article counts (CFU) | Percent Neutralization (%) |
|---|---|---|---|
| E. faecalis | 40 | 41 | 103 |
| C. albicans | 36 | 46 | 128 |
| S. mutans | ~7 | ~9 | ~129 |

The qualitative analysis, given here, confirms that the present invention is very useful and successful in its ability to disinfect the pulpal chamber from the test microorganisms (i.e., *E. faecalis, C. albicans*, and *S. mutans*). The qualitative analysis for all of the three test microorganisms at all of the time intervals had a greater than 99.9951% reduction of test microorganism. Neutralization of the microorganisms was successful, because all of the percentages for neutralization were over 70% which was needed for confirmation. Furthermore, in the recovery testing, there were no colonies forming units in any of the plates with any of the test microorganisms. Therefore, the microorganisms did not regenerate and did not reappear. The lack of the microorganisms present in the recovery results proves that the present invention is able to eradicate all the test materials/microorganisms during the instrumentation.

The above-reported test results prove that the composition, as provided by the present invention, provides antimicrobial activity against above organisms (i.e., *E. faecalis, C. albicans*, and *S. mutans*). Further, the tests show that the present invention, composition, or chemical depilatory provides unexpected results, thus proving its useful in endodontic applications for eradicating *E. faecalis, C. albicans* and *S. mutans* in a very short time. Furthermore, the test results prove that the present invention is able to prevent *E. faecalis, C. albicans*, and *S. mutans* from recovering. Therefore, these test results prove that the present invention is novel in its uses and has the ability to eradicate microorganisms in endodontic therapies. Further, the test results prove that the present invention is a novel single intra-canal medicament and as an effective bactericidal agent that kills *E. faecalis, S. mutans*, and *C. albicans*. The present invention may be useful to eradicate the microorganisms from other bony cavities having infections due to one of the microbes (e.g., *E. faecalis, S. mutans*, and *C. albicans*). If a bacteremia resulted after a dental procedure, these microbes may appear in other bony cavities or on orthopedic prosthesis that may benefit from the present invention's bactericidal ability.

Further, the test results prove that the present invention was successful in utilizing the chemical depilatory's ability to break disulfide bonds in bacteria and yeast to disrupt the functioning of the cells infected with the microbes. Therefore, disrupting the ability of the bacteria, yeast, and infected cells to function causes the cells to degrade facilitating the removal of tissues. Further, the test results prove that the present invention is able to disrupt the disulfide bonds in living cells and tissues.

The exemplary systems and methods of this present invention have been described in relation to a root canal treatment and removal of tissue from within a hard bony structure. However, to avoid unnecessarily obscuring the present invention, the preceding description omits a number of known structures and devices. This omission is not to be construed as a limitation of the scope of the claimed invention. Specific details are set forth to provide an understanding of the present invention. However it should be appreciated that the present invention may be practiced in a variety of ways beyond the specific detail set forth herein.

Also, while the flowcharts have been discussed and illustrated in relation to a particular sequence of events, it should be appreciated that changes, additions, and omissions to this sequence can occur without materially affecting the operation of the present invention.

A number of variations and modifications of the present invention can be used. It would be possible to provide for some features of the present invention without providing others.

While the foregoing is directed to embodiments of the present invention, other and further embodiments of the present invention may be devised without departing from the basic scope thereof. It is understood that various embodiments described herein may be utilized in combination with any other embodiment described, without departing from the scope contained herein. Further, the foregoing description is not intended to be exhaustive or to limit the present invention to the precise form disclosed. Modifications and variations are possible in light of the above teachings or may be acquired from practice of the present invention.

Certain exemplary embodiments may be identified by use of an open-ended list that includes wording to indicate the list items are representative of the embodiments and the list is not intended to represent a closed list exclusive of further embodiments. Such wording may include "e.g.," "etc.," "such as," "for example," "and so forth," "and the like," etc., and other wording as will be apparent from the surrounding context.

No element, act, or instruction used in the description of the present application should be construed as critical or essential to the present invention unless explicitly described as such. Also, as used herein, the article "a" is intended to include one or more items. Where only one item is intended, the term "one" or similar language is used. Further, the terms "any of" followed by a listing of a plurality of items and/or a plurality of categories of items, as used herein, are intended to include "any of," "any combination of," "any multiple of," and/or "any combination of multiples of" the items and/or the categories of items, individually or in conjunction with other items and/or other categories of items.

The present invention, in various embodiments, configurations, and aspects, includes components, methods, processes, systems and/or apparatus substantially as depicted and described herein, including various embodiments, subcombinations, and subsets thereof. Those of skill in the art will understand how to make and use the present invention after understanding the present disclosure. The present invention, in various embodiments, configurations, and aspects, includes providing devices and processes in the absence of items not depicted and/or described herein or in various embodiments, configurations, or aspects hereof, including in the absence of such items as may have been used in previous devices or processes, e.g., for improving performance, achieving ease and/or reducing cost of implementation.

The foregoing discussion of the present invention has been presented for purposes of illustration and description. The foregoing is not intended to limit the present invention to the form or forms disclosed herein. In the foregoing detailed description for example, various features of the present invention are grouped together in one or more embodiments, configurations, or aspects for the purpose of streamlining the disclosure. The features of the embodiments, configurations, or aspects of the present invention may be combined in alternate embodiments, configurations, or aspects other than those discussed above. This method of disclosure is not to be interpreted as reflecting an intention that the claimed invention requires more features than are expressly recited in each claim. Rather, as the following claims reflect, inventive aspects lie in less than all features of a single foregoing disclosed embodiment, configuration, or aspect. Thus, the following claims are hereby incorporated into this Detailed Description, with each claim standing on its own as a separate preferred embodiment of the present invention.

Moreover, though the description of the present invention has included description of one or more embodiments, configurations, or aspects and certain variations and modifications, other variations, combinations, and modifications are within the scope of the present invention, e.g., as may be within the skill and knowledge of those in the art, after understanding the present disclosure. It is intended to obtain rights which include alternative embodiments, configurations, or aspects to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A treatment composition for disinfecting, degrading and decomposing diseased, cancerous or dysplastic tissues located at a site within a hard bony cavity and for killing microorganisms at said site, when applied to said tissues and said microorganisms at said site;
   wherein said treatment composition consists of water, calcium hydroxide or sodium hydroxide, or blends thereof and a thioglycolate; and
   wherein said microorganisms comprise at least one member selected from the group consisting of *Enterococcus faecalis, Candida albicans* and *Streptococcus mutans*.

2. The treatment composition according to claim 1, wherein the thioglycolate is potassium thioglycolate.

3. A treatment composition for disinfecting, degrading and decomposing diseased, cancerous or dysplastic tissues located at a site within a hard bony cavity and for killing microorganisms at said site, when applied to said tissues and said microorganisms at said site;
   wherein said treatment composition consists of water, calcium hydroxide or sodium hydroxide, or blends thereof, sodium hypochlorite and a thioglycolate;
   wherein said treatment composition contains up to 5.25% of said sodium hypochlorite; and
   wherein said microorganisms comprise at least one member selected from the group consisting of *Enterococcus faecalis, Candida albicans* and *Streptococcus mutans*.

4. The treatment composition according to claim 3, wherein the thioglycolate is potassium thioglycolate.

5. A treatment composition for disinfecting, degrading and decomposing diseased, cancerous or dysplastic tissues located at a site within a hard bony cavity and for killing microorganisms at said site, when applied to said tissues and said microorganisms at said site;
   wherein said treatment composition is alkaline and consists of water, calcium hydroxide or sodium hydroxide or blends thereof, sodium hypochlorite, potassium thioglycolate;
   wherein said microorganisms comprise at least one member selected from the group consisting of *Enterococcus faecalis, Candida albicans* and *Streptococcus mutans*.

6. The treatment composition according to claim 5 wherein said composition is used as a rinse at a target site.

7. The treatment composition according to claim 1, wherein said composition is used as a rinse at a target site.

* * * * *